US010206886B2

(12) United States Patent
Gainza Lafuente et al.

(10) Patent No.: US 10,206,886 B2
(45) Date of Patent: Feb. 19, 2019

(54) LIPID NANOPARTICLES FOR WOUND HEALING

(71) Applicant: Praxis Biopharma Research Institute, Miñano (Alava) (ES)

(72) Inventors: Eusebio Gainza Lafuente, Miñano (ES); Garazi Gainza Lucea, Vitoria-Gasteiz (ES); Silvia Villullas Rincón, Miñano (ES); Marta Pastor Navarro, Miñano (ES); Oihane Ibarrola Moreno, Miñano (ES); Gorka Alonso Hornes, Miñano (ES); Angel Del Pozo Pérez, Miñano (ES); Rosa María Hernández Martín, Vitoria-Gasteiz (ES); Manuela Igartua Olaechea, Vitoria-Gasteiz (ES); José Luis Pedraz Muñoz, Vitoria-Gasteiz (ES)

(73) Assignee: PRAXIS BIOPHARMA RESEARCH INSTITUTE, Miñano (Alava) (ES)

(*) Notice: Subject to any disclaimer, the term of this patent is extended or adjusted under 35 U.S.C. 154(b) by 0 days.

(21) Appl. No.: 14/902,766

(22) PCT Filed: Jul. 3, 2014

(86) PCT No.: PCT/ES2014/070541
§ 371 (c)(1),
(2) Date: Jan. 4, 2016

(87) PCT Pub. No.: WO2015/001163
PCT Pub. Date: Jan. 8, 2015

(65) Prior Publication Data
US 2016/0199447 A1 Jul. 14, 2016

(30) Foreign Application Priority Data

Jul. 4, 2013 (EP) .................................. 13382275

(51) Int. Cl.
*A61K 9/51* (2006.01)
*A61K 38/18* (2006.01)
*A61K 38/17* (2006.01)

(52) U.S. Cl.
CPC .......... *A61K 9/5123* (2013.01); *A61K 9/5192* (2013.01); *A61K 38/1729* (2013.01); *A61K 38/18* (2013.01); *A61K 38/1808* (2013.01)

(58) Field of Classification Search
None
See application file for complete search history.

(56) References Cited

U.S. PATENT DOCUMENTS

| | | | | |
|---|---|---|---|---|
| 5,034,375 A * | 7/1991 | Antoniades | ........ | A61K 38/1808 514/7.6 |
| 2007/0149448 A1* | 6/2007 | Stahle-Backdahl | ........................ | A61K 9/1272 514/9.4 |
| 2016/0113995 A1* | 4/2016 | Gainza Lafuente | ... | A61K 38/12 514/21.1 |

FOREIGN PATENT DOCUMENTS

| | | | |
|---|---|---|---|
| GB | 2415903 | 1/2006 | |
| WO | 9118999 | 12/1991 | |
| WO | 9939700 | 8/1999 | |
| WO | wo9939700 A1 * | 8/1999 | ............... A61K 9/51 |
| WO | 2005120469 | 12/2005 | |
| WO | 2015001163 A2 | 1/2015 | |

OTHER PUBLICATIONS

Trafny, Elzbieta Anna et al, "Anti-pseutomonal activity of collagen sponge with liposomal polymyxin b." Pharmacol. Res. (1996) 33(1) p. 62-64.*
The Quantum health webpage, https://www.quantumhealth.com/pages/how-to-relieve-dry-cracked-skin, downloaded Apr. 17, 2017.*
Ulubayram, Kezban et al, "EGF containing gelatin-based wound dressings." Biomaterials (2001) 22 p. 1345-1356.*
Borgia et al.; "Lipid Nanoparticles for Skin Penetration Enhancement—Correlation to Drug Localization Within the Particle Matrix as Determinded by Fluorescence and Parelectric Spectroscopy"; Journal of Controlled Release, vol. 110; 2005; pp. 151-163.
Chen et al, "Effects of Lipophilic Emulsifiers on the Oral Administration of Lovastatin from Nanostructured Lipid Carriers: Physicochemical Characterization and Pharmacokinetics"; European Journal of Pharmaceutics & Biopharmaceutics, 74; 2010; p. 474-482.
Cotran et al.; "Inflammation and Repair"; McGraw Hill Interamericana; 2010; pp. 29-73.
Heilborn et al.; "The Cathelicidin Anti-Microbial Peptide LL-37 is Involved in Re-Epithelialization of Human Skim Wounds and is Lacking in Chronic Ulcer Epithelium"; The Journal of Investigative Dermatology, vol. 120, No. 3; Mar. 2003; pp. 379-389.
International Search Report for International Application No. PCT/ES2014/070541; International Filing Date Jul. 3, 2014; dated Feb. 18, 2015; 12 pages.
Kuchler et al.; "Nanoparticles for Skin Penetration Enhancement—A Comparison of a Dendritic Core-Multishell-Nanotransporter and sPolid Lipid Nanoparticles"; European Journal of Pharmaceutics and Biopharmaceutics, vol. 71; 2009; pp. 243-250.
Lee et al.; "Apoptotic Epidermal Growth Factor (EGF)-Conjugated Block Copolymer Micelles as a Nanotechnology Platform for Targeted Combination Therapy"; Molecular Pharmaceutics, vol. 4, No. 5; 2007; pp. 769-781.

(Continued)

*Primary Examiner* — Fred H Reynolds
(74) *Attorney, Agent, or Firm* — Cantor Colburn LLP

(57) ABSTRACT

The present invention refers to lipid nanoparticles comprising a growth factor and/or an antimicrobial peptide and to the method for their preparation. Moreover, it refers to pharmaceutical compositions comprising such lipid nanoparticles, and a pharmaceutical acceptable carrier. Finally, it also refers to said pharmaceutical composition for its use as medicament and for its use in promoting wound healing, particularly by topical administration.

17 Claims, 18 Drawing Sheets
Specification includes a Sequence Listing.

(56) References Cited

OTHER PUBLICATIONS

Manjunath et al.; "Solid Lipid Nanoparticles as Drug Delivery Systems"; Methods Find Exp. Clin. Pharmacol, vol. 27, No. 2; 2005; pp. 1-20.

Michaels et al.; "Db/Db Mice Exhibit Severe Wound-Healing Impairments Compared with Other Murine Diabetic Strains in a Silicone-Splinted Excisional Wound Model"; Wound Repair and Regeneration, vol. 15; 2007; pp. 665-670.

Morioka-Fujimoto et al.; "Modified Enterotoxin Signal Sequences Increase Secretion Level of the Recombinant Human Epidermal Growth Factor in *Escherichia coli*"; The Journal of Biological Chemistry, vol. 266, No. 3; Jan. 25, 1991; pp. 1728-1732.

Muller et al.; "Solid Lipid Nanoparticles (SLN) and Nanostructured Lipid Carriers (NLC) in Cosmetic and Dermatological Preparations"; Advanced Drug Delivery Reviews 54, Suppl. 1; 2002; pp. 131-155.

Sinha et al.; "Effects of Steel Scalpel, Ultrasonic Scalpel, CO2 Laser, and Monopolar and Bipolar Electrosurgery on Wound Healing in Guinea Pig Oral Mucosa"; The Laryngoscope, vol. 113; Feb. 2003; pp. 228-236.

Zhou et al.; Effects of Leukemia Inhibitory Factor on Proliferation and Odontoblastic Differentiation of Human Dental Pulp Cells; Basic Research—Biology, JOE, vol. 37, No. 6; Jun. 2011; pp. 819-824.

\* cited by examiner

LIPID NANOPARTICLES FOR WOUND HEALING

CROSS REFERENCE TO RELATED APPLICATIONS

This is a U.S. national stage of application No. PCT/ES2014/070541, filed on 3 Jul. 2014. Priority under 35 U.S.C. § 119(a) and 35 U.S.C. § 365(b) is claimed from European Application No. 13382275.9 filed on 4 Jul. 2013, the disclosure of which is also incorporated herein in its entirety by reference.

FIELD OF THE INVENTION

The invention refers to lipid nanoparticles and their use as pharmaceutical compositions for wound healing, in particular as nanoparticle suspensions, dressings or gels for topical application.

BACKGROUND OF THE INVENTION

Chronic wound treatment has become a major problem for health care systems worldwide, representing a great economic and public health challenge. The current increase of risk factors such as, ageing population, smoking, diabetes and obesity can complicate and slow down the wound healing process, causing difficult-to-heal wounds.

Several palliative treatments including hyperbaric oxygen, negative pressure and surgical debridement are currently being used for the treatment of chronic wounds in elderly people. In addition, a wide range of commercial synthetic dressings for the treatment of chronic ulcers are available in the market, although showing a limited healing efficacy.

The epidermal growth factor (EGF) plays an important role in tissue regeneration and repair by stimulating cell migration, differentiation and proliferation, and also by promoting granulation tissue formation. From a clinical point of view, EGF has been used to enhance wound healing, especially in diabetic foot ulcers. Evidences of the beneficial effects of topical EGF application in low-grade, neuropathic ulcers have been shown in clinical trials; however, the effect of topical EGF formulation can be abated, especially in high-grade wounds, since an increased protease activity has been identified in this type of wounds. Rengen-D 150™ is a gel containing 150 µg/g of recombinant human epidermal growth factor (rhEGF) manufactured in India for the treatment of grade I or II diabetic ulcers. It requires twice daily administration, for an average treatment time of 6 weeks. Heberprot®, a lyophilised formulation containing 75 µg of rhEGF, is administered three times weekly by intralesional injections. It is marketed in Algeria, Argentina, Colombia, Cuba, the Dominican Republic and Venezuela. A pilot study carried out in 20 diabetic patients demonstrated Heberprot® as a feasible and safe treatment to promote healing of chronic wounds in patients with full thickness ulcers. However, rhEGF short half-life requires continuous exposure (at least 6-12 hours) to enhance the mitogenic effect on epithelial cells. Therefore, in order to achieve a significant therapeutic effect in wound healing, it is necessary to optimise the administration of growth factors such as rhEGF, in terms of dose, delivery system and safety. For that purpose, Chu et al., 2010 (*Nanotechnology promotes the full-thickness diabetic wound healing effect of recombinant human epidermal growth factor in diabetic rats*", Wound Repair Regen 2010; 15:499-505) have developed a method to prepare nanoparticles of the polymer poly(lactic-co-glycolic acid) (PLGA) with a 2% rhEGF content. rhEGF encapsulation efficiency was 85.6% and presented a controlled release of biologically active rhEGF for up to 24 hours. Topical application once daily of these nanoparticles on full-thickness wounds induced in diabetic rats promoted higher fibroblast proliferation levels and fastest healing rates, compared with non-encapsulated rhEGF.

In addition, patent EP 1 987 817 B1 claims the process of producing polymeric microspheres containing rhEGF for intralesional infiltration into the lower limbs of diabetic patients to prevent diabetic limb amputation. Developed microspheres with a 1.6-2.4% rhEGF content showed a rhEGF controlled release of 5 and 10 µg per day during 14 days and a faster injury healing in humans compared with equivalent amounts of non-encapsulated rhEGF.

Surprisingly, the inventors have developed lipid nanoparticles comprising epidermal growth factor with high encapsulation efficiencies, that applied in a topical formulation twice a week, improve wound healing.

BRIEF SUMMARY OF THE INVENTION

According to one aspect, the application refers to a lipid nanoparticle (nanoparticle of the invention) that comprises at least one solid lipid at room temperature, at least one non-ionic surfactant, and one growth factor.

According to a further aspect, the application refers to a method for the preparation of the lipid nanoparticle of the invention characterized by comprising the following steps:
(i) preparing an aqueous solution comprising a non-ionic surfactant,
(ii) preparing a lipophilic solution comprising a solid lipid at room temperature in an organic solvent,
(iii) adding the aqueous solution (i) to the lipophilic solution (ii), subjecting the resulting mixture to sonication until obtaining an emulsion,
(iv) evaporating the organic solvent of the obtained emulsion in (iii), and
(v) collecting the lipid nanoparticles,
wherein the growth factor is added to the solution (ii).

According to a further aspect, the application refers to a pharmaceutical composition (pharmaceutical composition of the invention) comprising the lipid nanoparticle of the invention and a pharmaceutical carrier.

According to a further aspect, the application refers to the lipid nanoparticle of the invention and to the pharmaceutical composition comprising it, for its use as a medicament, and for its use in promoting wound healing.

Other objects, features, advantages and aspects of the present application will become apparent to those skilled in the art from the following description and appended claims.

μg. Data shown as means±standard deviation (S.D.) *Significantly greater than untreated control (*p<0.05, p<0.01 and *p<0.001); ■Significantly greater than empty MS control (■p<0.05, ■■p<0.01 and ■■■p<0.001); ●Significantly greater than empty SLN (●p<0.05, ●●p<0.01 and ●●●p<0.001); ▼Significantly greater than empty NLC (▼p<0.05, ▼▼p<0.01 and ▼▼▼p<0.001); °Significantly greater than free rhEGF (°p<0.05, °°p<0.01 and °°°p<0.001); ◊Significantly greater than rhEGF-MS 75 μg (◊p<0.05, ◊◊p<0.01 and ◊◊◊p<0.001); ▲Significantly greater than rhEGF-SLN 10 μg (▲p<0.05, ▲▲p<0.01 and ▲▲▲p<0.001).

Figure 4A:
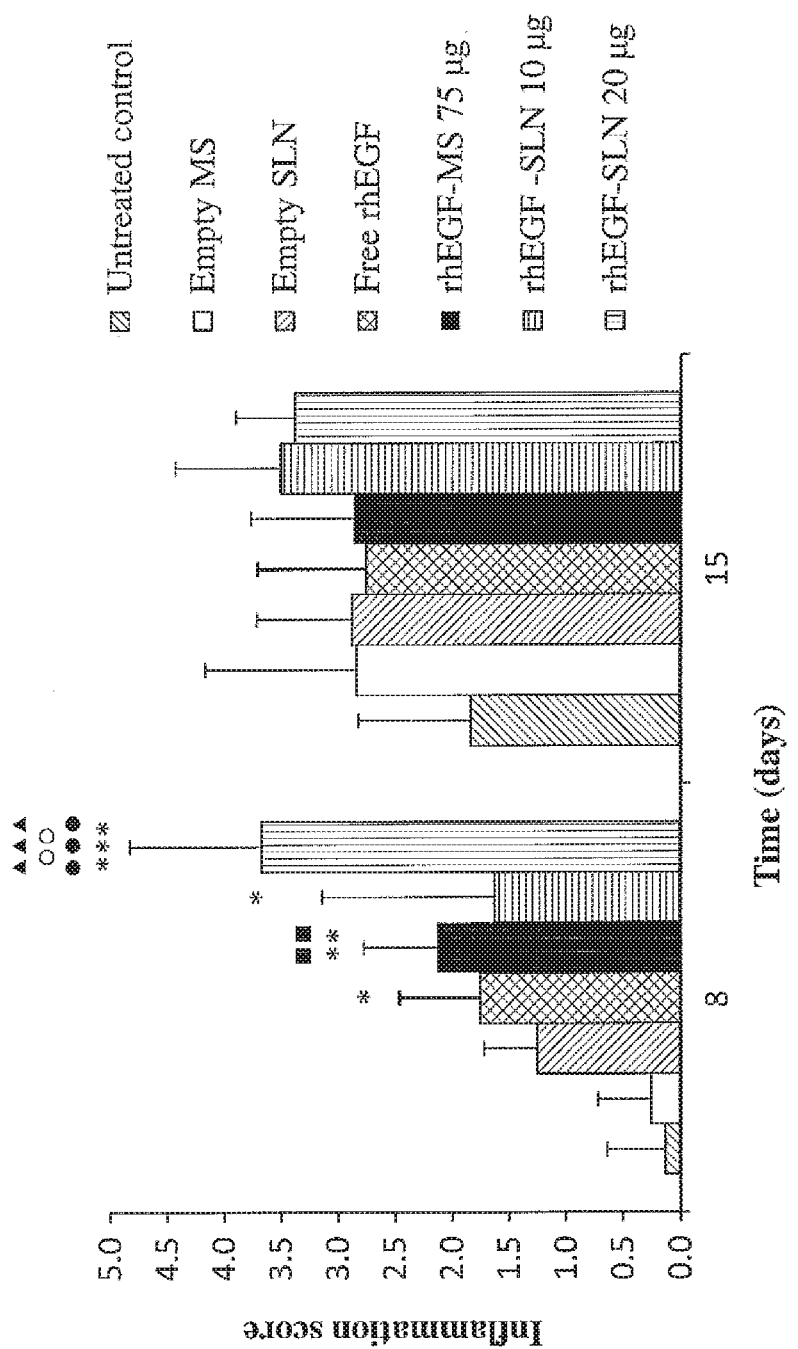
Figure 4B:
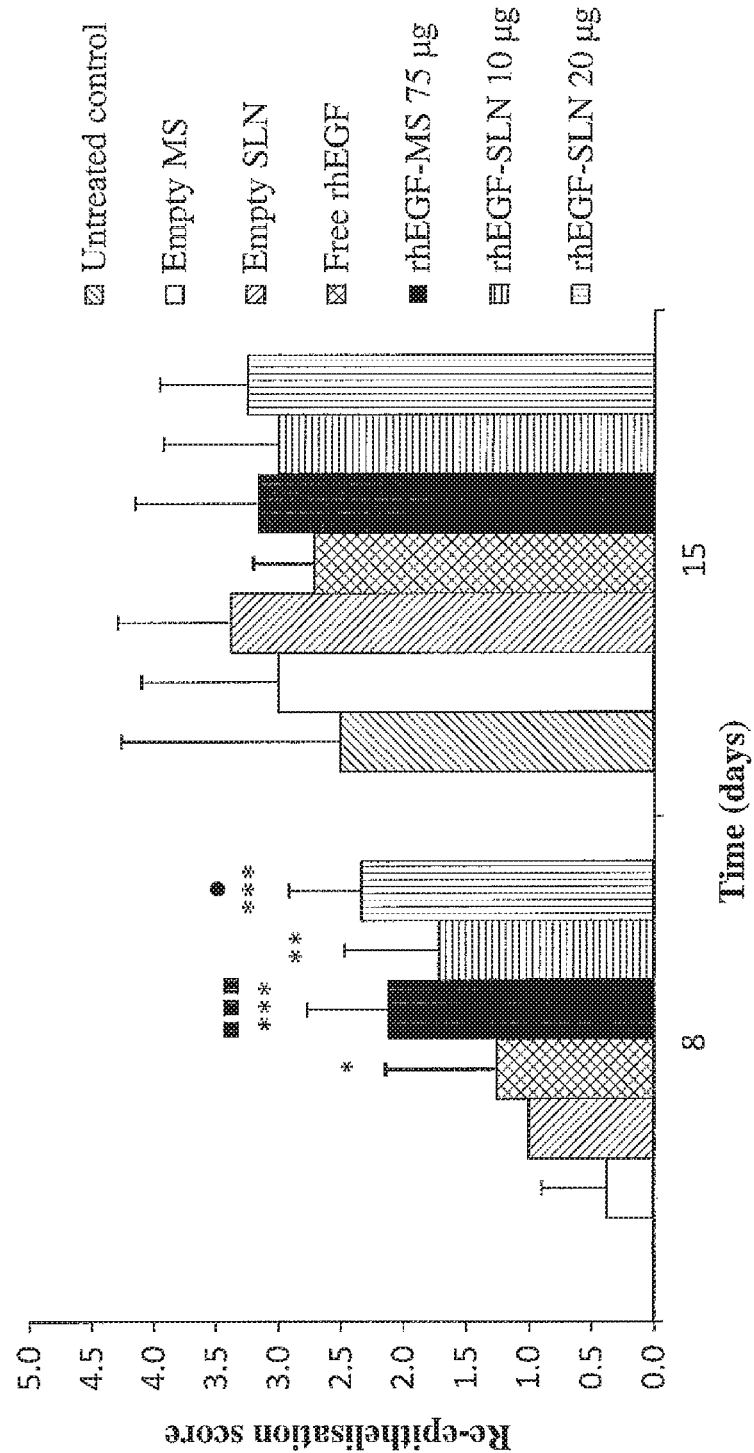
Figure 4C:
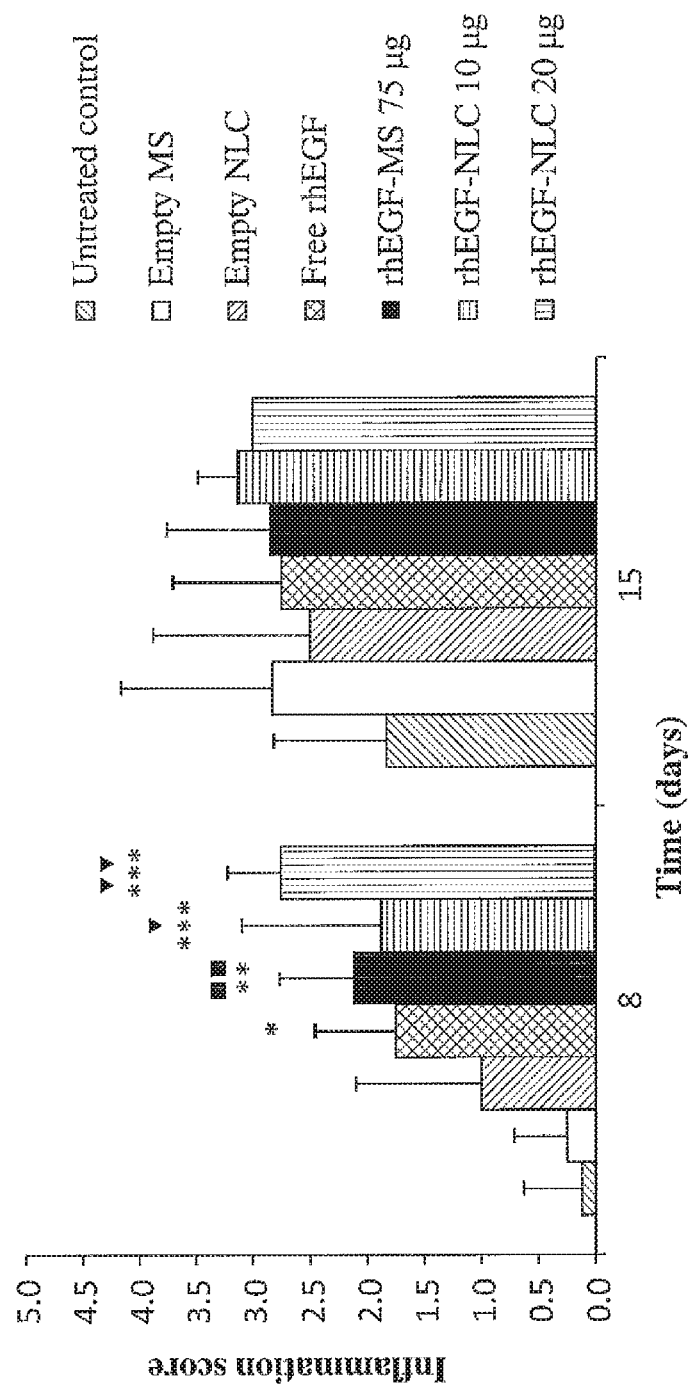
Figure 4D:
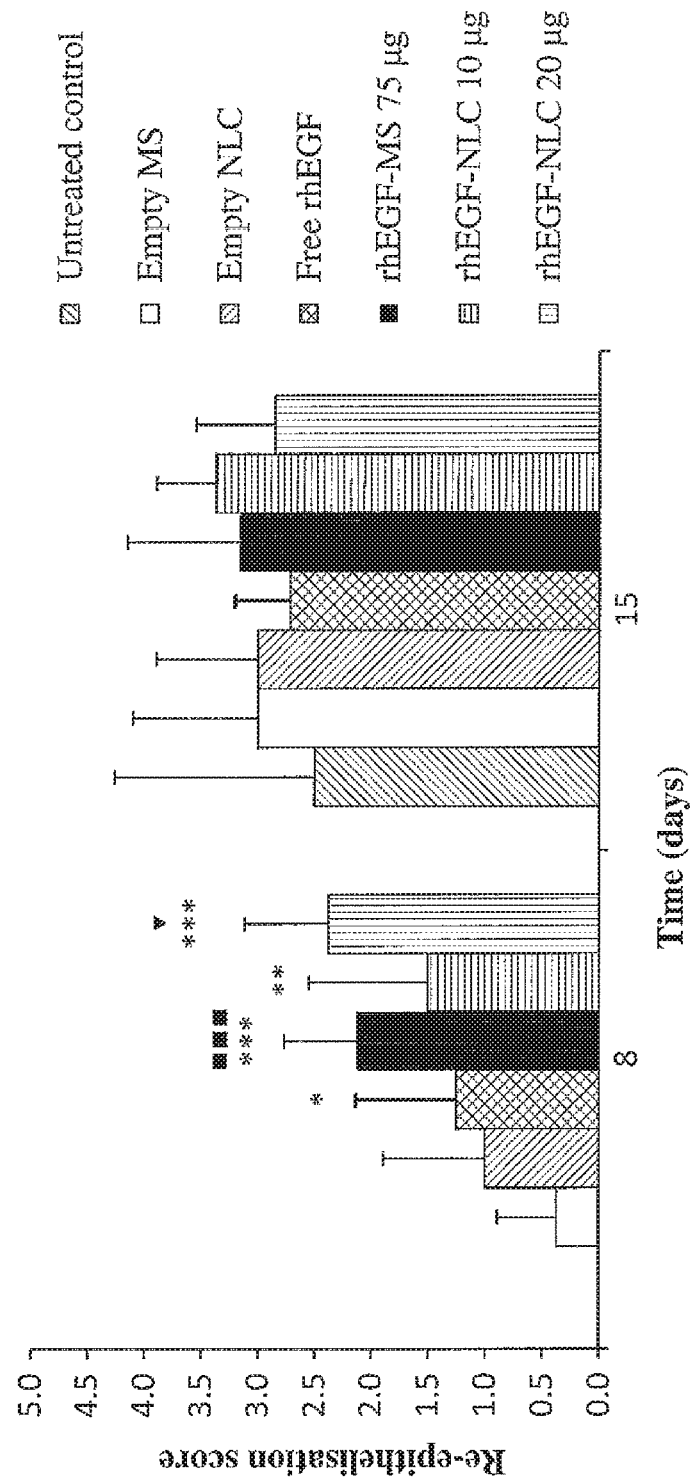

FIGS. 4A and 4C show a graphic representation of the in vitro effect of rhEGF-loaded lipid nanoparticles on the inflammation score (A, C) and FIGS. 4B and 4D show a graphic representation of the in vitro effect of rhEGF-loaded lipid nanoparticles on the re-ephitelization score (B, D).

Data shown as means±S.D. *Significantly greater than untreated control (*p<0.05, p<0.01 and *p<0.001); ■Significantly greater than control empty MS (■p<0.05, ■■p<0.01 and ■■■p<0.001); ●Significantly greater than empty SLN (●p<0.05, ●●p<0.01 and ●●●p<0.001); ▼Significantly greater than empty NLC (▼p<0.05, ▼▼p<0.01 and ▼▼▼p<0.001); °Significantly greater than free rhEGF (°p<0.05, °°p<0.01 and °°°p<0.001); ◊Significantly greater than rhEGF-MS 75 μg (◊p<0.05, ◊◊p<0.01 and ◊◊◊p<0.001); ▲Significantly greater than rhEGF-SLN 10 μg (▲p<0.05, ▲▲p<0.01 and ▲▲▲p<0.001).

Figure 5A:
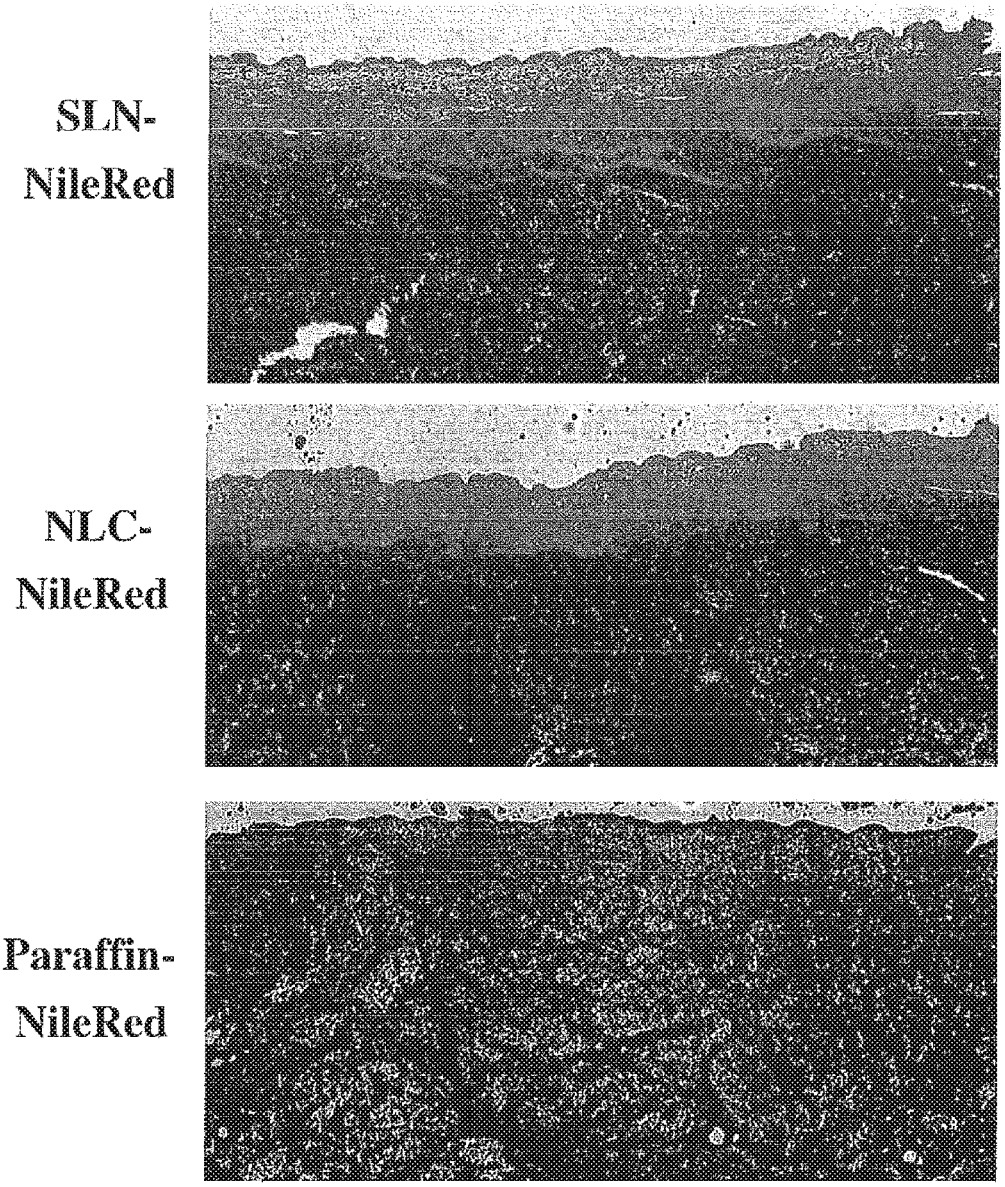
Figure 5B:
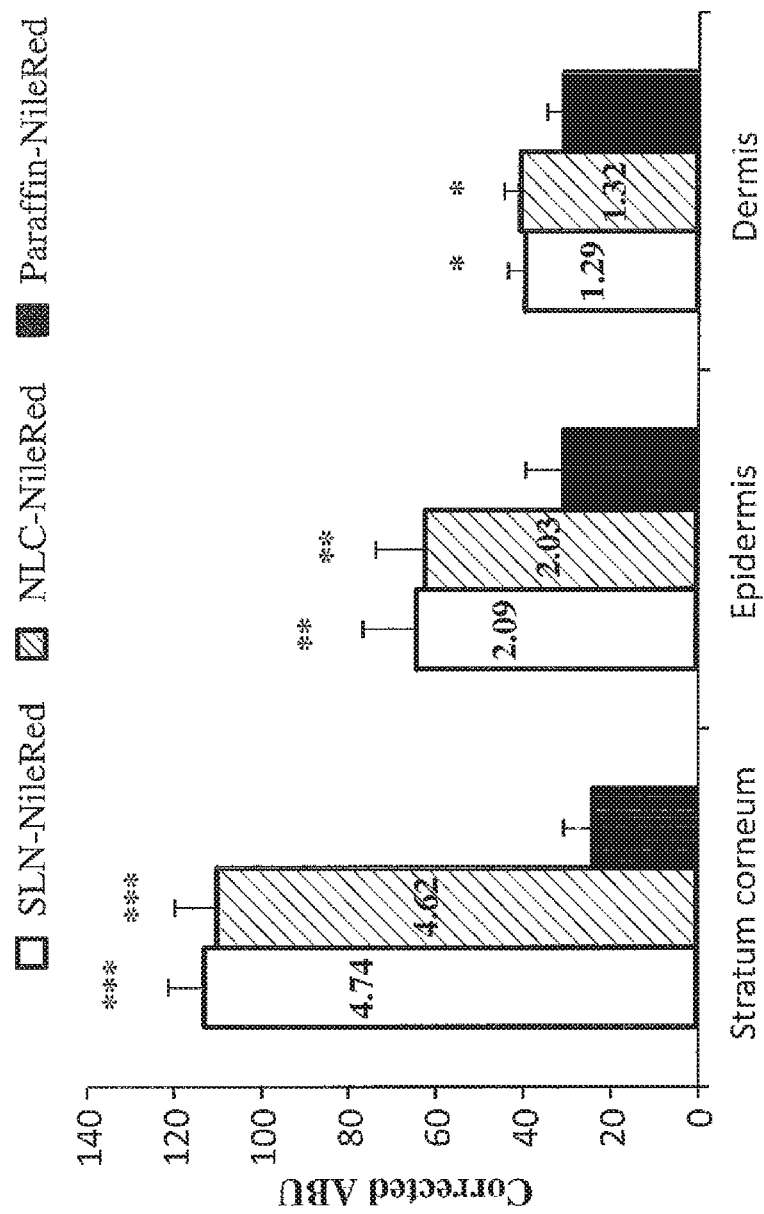

FIG. 5A shows micrographs (A) and FIG. 5B shows a graphic representation (B) of the coetaneous uptake of SLN-NileRed, NLC-NileRed and Paraffin-NileRed (arbitrary pixel brightness values (ABU) corrected for the background fluorescence in the stratum corneum, epidermis and dermis). *Significantly greater than Paraffin-NileRed (*p<0.05, p<0.01 and *p<0.001). The inserted numbers give the respective enhancement of penetration over paraffin cream (PEE).

Figure 6:
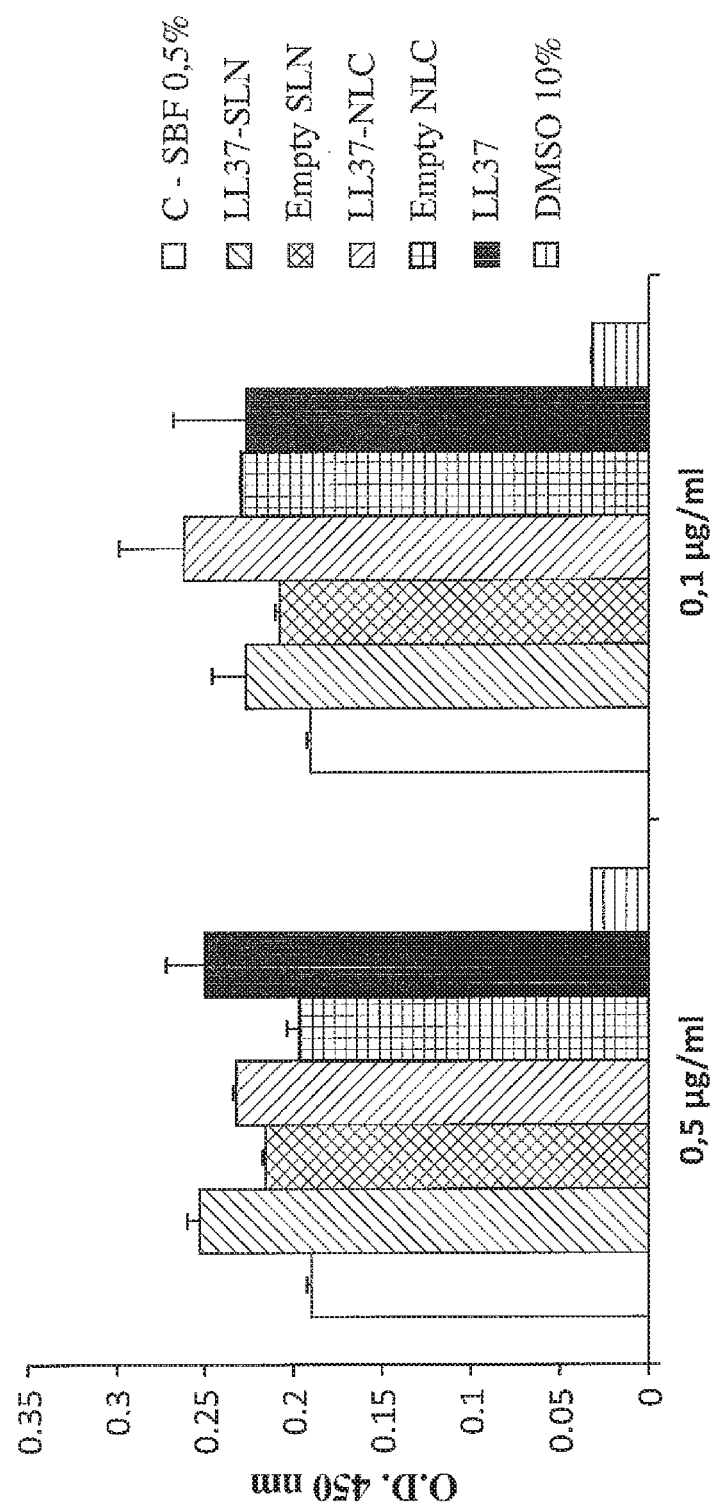

FIG. 6 shows a graphic representation of the in vitro effect of the LL37-loaded lipid nanoparticles on cell proliferation.

Figure 7A:
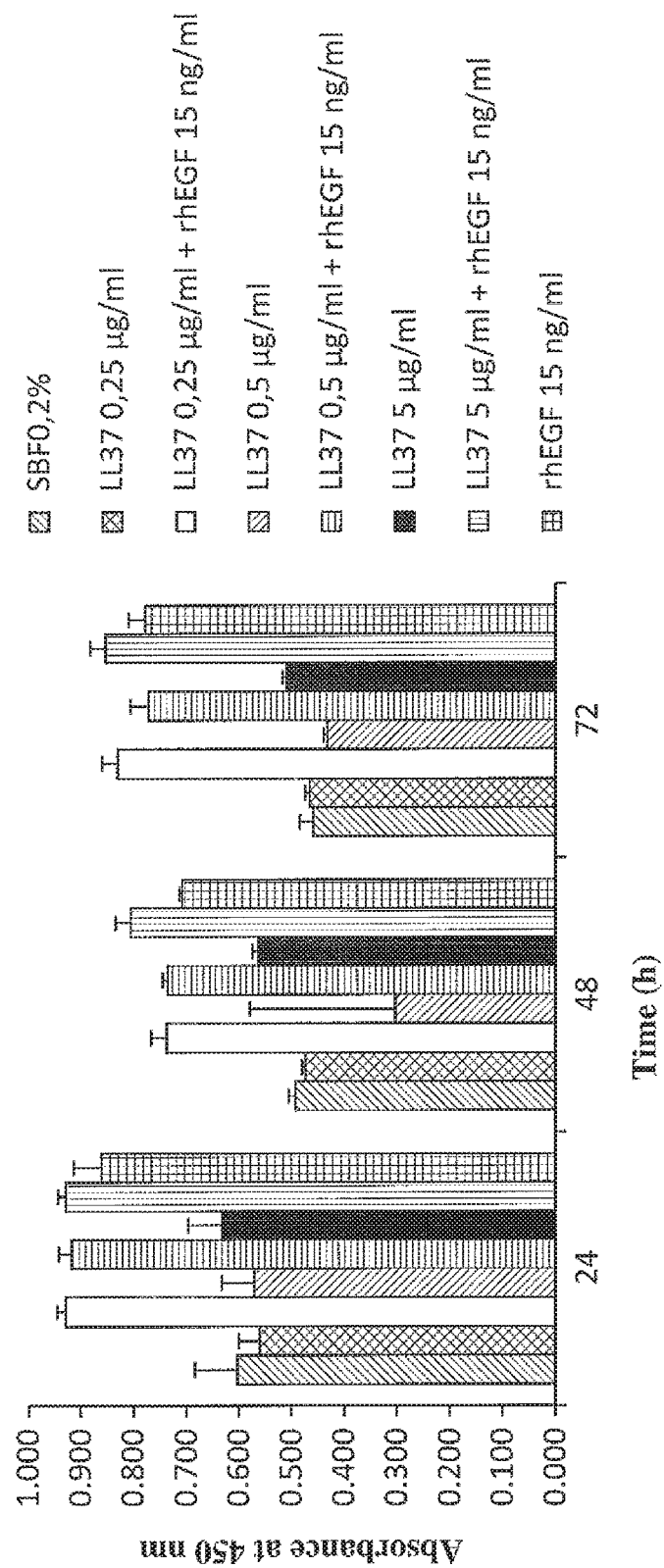
Figure 7B:
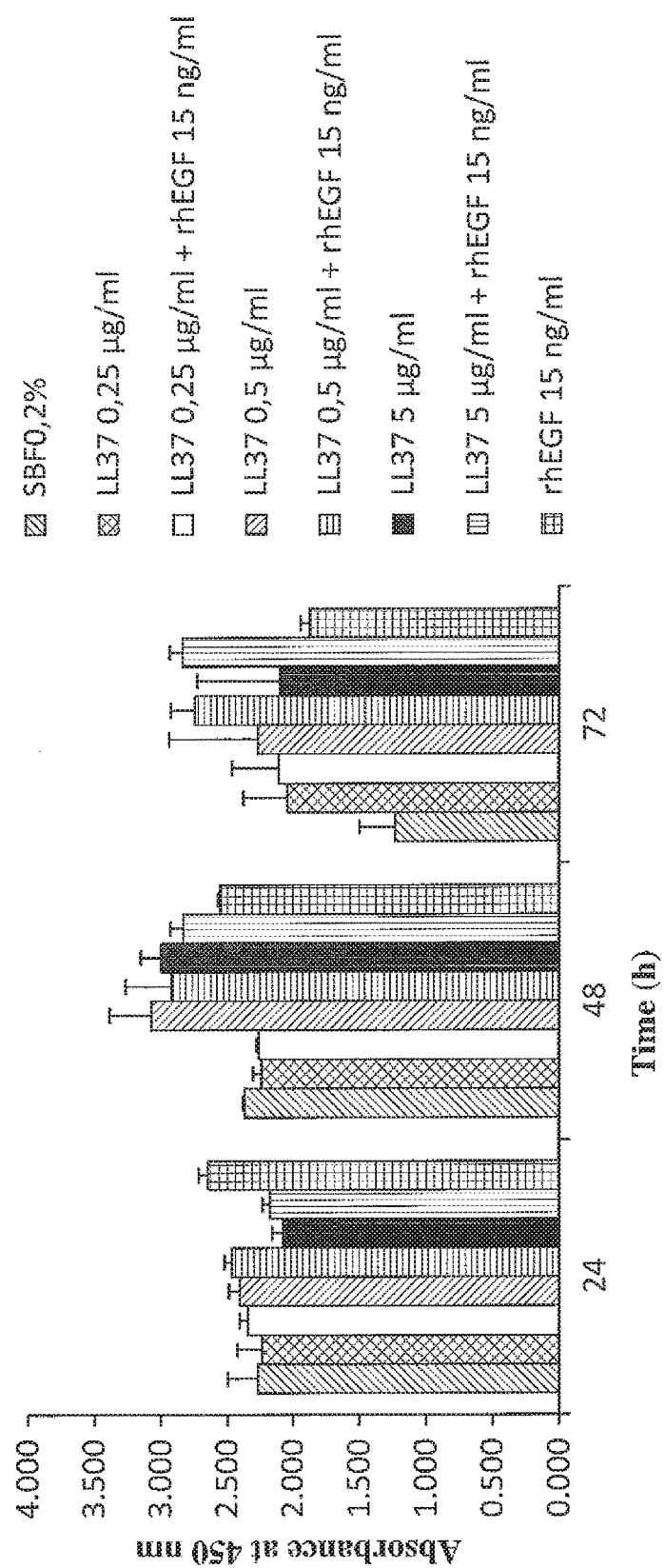

FIGS. 7A and 7B show a graphic representation of the in vitro effect of the combination of rhEGF and LL37 on cell proliferation.

Figures 8A, 8B:
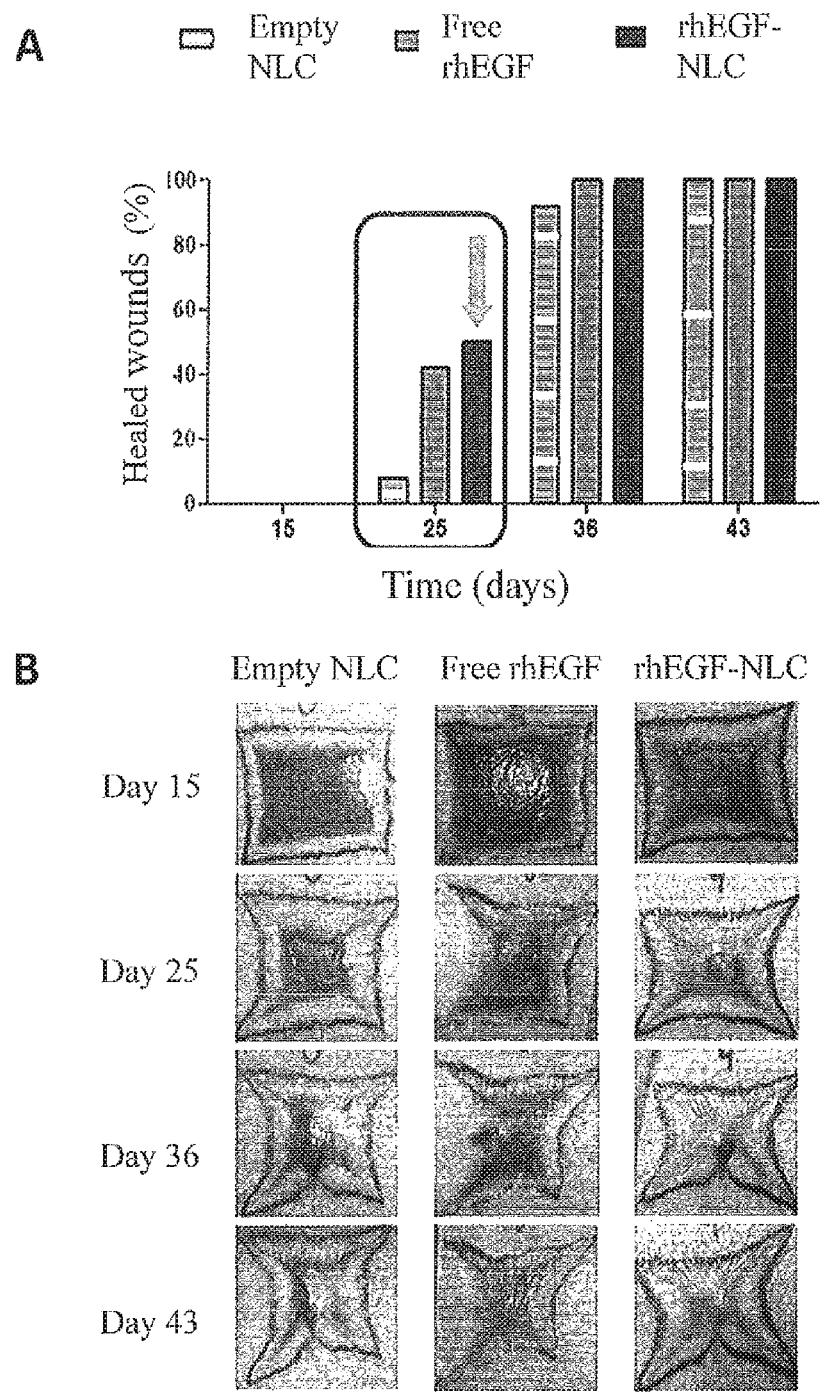

FIG. 8A shows a graphic representation of the in vivo effect of empty NLC, free rhEGF and rhEGF-NLC 20 μg on the wound closure in pigs on days 15, 25, 36 and 43 and FIG. 8B shows photographs of the wounds in pigs treated with empty NLC, free rhEGF and rhEGF-NLC 20 μg.

Figures 9A, 9B:
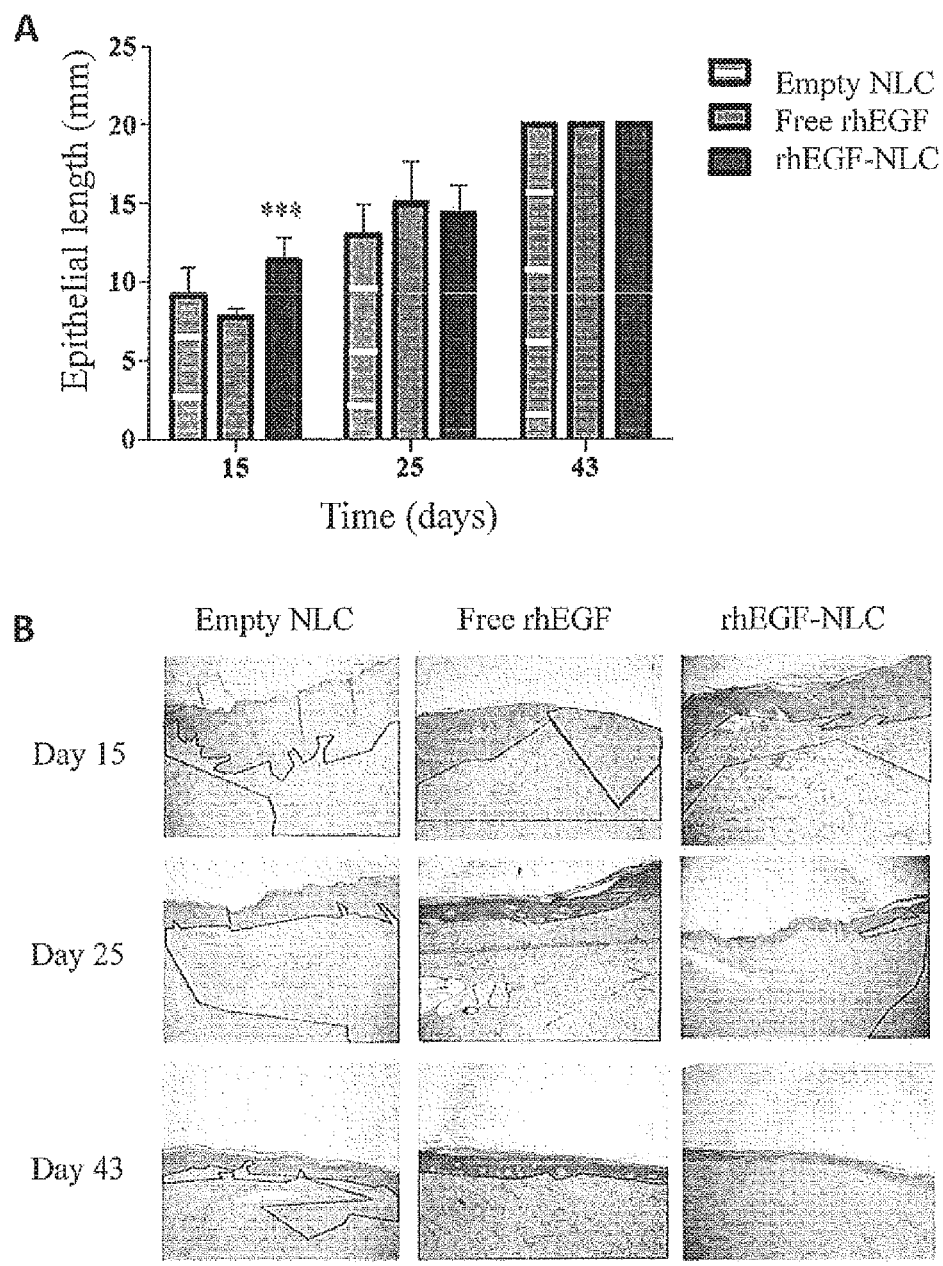

FIG. 9A shows a graphic representation of the epithelial length in the different groups studied (empty NLC, free rhEGF and rhEGF-NLC 20 μg) on days 15, 25, and 43 and FIG. 9B shows histological images of the wounds on days 15, 25 and 43. Data shown as means±S.D. ***Significantly greater than empty NLC and free rhEGF (p<0.001).

Figure 10A:
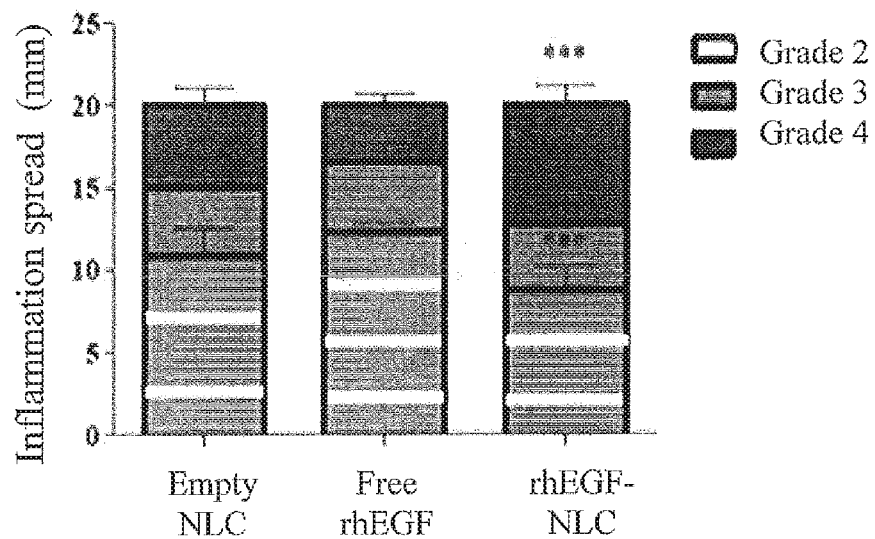
Figure 10B:
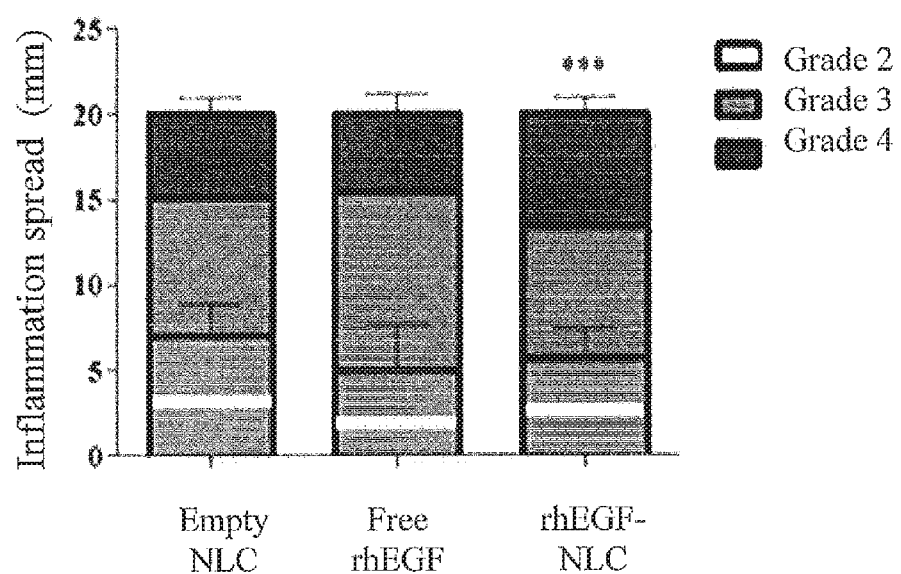
Figure 10C:
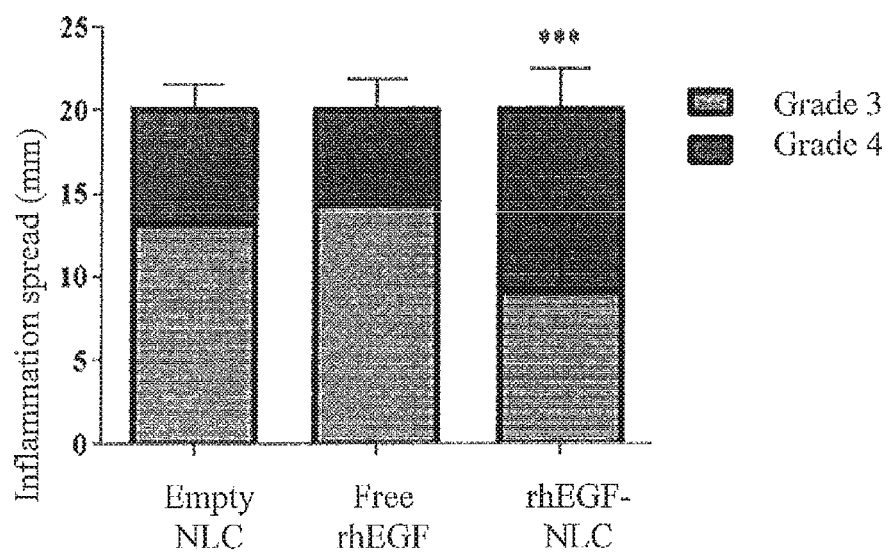

FIG. 10A shows a graphic representation of the wound healing extension (mm) on day 15, FIG. 10B shows a graphic representation of the wound healing extension (mm) on day 25, and FIG. 10C shows a graphic representation of the wound healing extension (mm) on day 43. Data shown as means±S.D. ***p<0.001 compared with the empty NLC and free rhEGF groups.

DETAILED DESCRIPTION OF THE INVENTION

A first aspect of the present invention refers to a lipid nanoparticle characterized by comprising at least one solid lipid at room temperature, at least one non-ionic surfactant, and one growth factor.

It must be noted that as used in the present application, the singular forms "a", "an" and "the" include plural referents unless the context clearly dictates otherwise.

In the context of the present invention, lipid nanoparticles are referred to particles in the nanometer range possessing a solid matrix. The matrix is composed of lipids being solid at room temperature, but also at body temperature. In the case of solid lipid nanoparticles (SLN) the matrix consists of a solid lipid only. In case of nanostructured lipid carriers (NLC) the matrix consists of a blend of solid lipids with liquid lipids (oils), but this blend being also solid at room temperature and also at body temperature (Muller et al., 2002, *Solid lipid nanoparticles (SLN) and nanostructured lipid carriers (NLC) in cosmetic and dermatological preparations*. Advanced Drug Delivery Reviews 54 (1) S131-S155). The term "growth factor-loaded" refers to the growth factor embedded or encapsulated in the matrix of the nanoparticle. Thus, in one particular embodiment, the lipid nanoparticles are SLN and in another particular embodiment, the lipid nanoparticles are NLC. Thus, in a particular embodiment the lipid nanoparticles are SLN or NLC.

In a particular embodiment, the growth factor is selected from the group consisting of a growth factor belonging to the epidermal growth factor (EGF) family, transforming growth factor beta (TGF-beta) family, fibroblast growth factor (FGF) family, vascular endothelial growth factor (VEGF), granulocyte macrophage colony stimulating factor (GM-CSF), platelet-derived growth factor (PDGF), connective tissue growth factor (CTGF), tumor necrosis factor-alpha family (TNFα), insulin-like growth factors (IGF). Preferably, the growth factor belongs to the epidermal growth factor (EGF) family, and more preferably the growth factor is the epidermal growth factor (EGF). In a particular embodiment, the lipid nanoparticles are EGF-loaded SLN (also referred as EGF-SLN hereinafter) and/or EGF-loaded NLC (also referred as EGF-NLC hereinafter). In a particular embodiment of the invention, the epidermal growth factor is the recombinant human epidermal growth factor (rhEGF). Said rhEGF can be obtained commercially (Peprotech, Promega, Pharmchem, etc.) or produced by means of recombinant DNA technology, as described for example in Marioka-Fujimoto et al. (*Modified enterotoxin signal sequences increase secretion level of the recombinant human epidermal growth factor in Escherichia coli*. J Biol Chem. 1991 Jan. 25; 266(3): 1728-32), or in the patent application WO 91/18999 A1. In a particular embodiment, the lipid nanoparticle of the invention has a proportion of growth factor, in particular EGF, comprised between 0.01% and 20% by weight with respect to the total weight of the lipid nanoparticle, preferably between 0.1% and 10% by weight, and more preferably between 0.5% and 5% by weight with respect to the total weight of the lipid nanoparticle.

As mentioned above, the lipid nanoparticles of the present invention comprise at least one solid lipid at room temperature. In the context of the present invention, "solid lipid at room temperature" is understood as the lipid being solid under 45° C., being able to be saturated or unsaturated. Said definition includes mono-, di-, or triglycerides, fatty acids, steroids and waxes. Likewise, derivatives of these fatty acids, understood as those compounds produced as a result of the reaction of the acid group with alcohols or amines such as, for example, the esters or amides of said fatty acids, can be used. Thus, in a particular embodiment, the solid lipid at room temperature is selected from acylglycerides, saturated fatty acids with a chain of at least 10 carbon atoms or derivatives thereof and mixtures thereof. In a preferred embodiment the acylglycerides are selected from glyceryl palmitostearate (Precirol® ATO5), glyceryl monostearate (Imwitor® 900) and glyceryl behenate (Compritol® 888ATO). In a more preferred embodiment, the lipid component is glyceryl palmitostearate (Precirol® ATO5).

In a particular embodiment of the invention, the lipid nanoparticle has a proportion of solid lipid comprised between 1% and 40% by weight with respect to the total weight of the lipid nanoparticle, preferably between 5% and 15.

As mentioned above, the lipid nanoparticles of the invention also comprise a non-ionic surfactant. The term "non-ionic surfactant" is understood as that compound that have a hydrophobic part and a hydrophilic part which allows producing an emulsion. In a particular embodiment of the present invention the non-ionic surfactant is selected from polysorbates, polyethylene glycol copolymers and polypropylene glycol copolymers, and mixtures thereof. In a particular embodiment, the non-ionic surfactant is selected from the group consisting of Tween, Span, Poloxamer and mixtures thereof. In a preferred embodiment, the non-ionic surfactant is Tween 80, and in another preferred embodiment, the non-ionic surfactant is a mixture of Tween 80 and Poloxamer.

In a particular embodiment of the invention, the proportion of non-ionic surfactant is comprised between 0.01% and 10% by weight with respect to the total weight of the lipid nanoparticle, preferably between 0.05% and 5%.

In a particular embodiment of the invention, the lipid nanoparticle of the invention comprises between 1% and 40% of the solid lipid at room temperature, between 0.01% and 10% of the non-ionic surfactant, and between 0.01% and 20% of the growth factor, all percentages given by weight with respect to the total weight of the lipid nanoparticle.

In a particular embodiment, the lipid nanoparticle of the invention can optionally be presented as lyophilized or desiccated product.

In a second aspect, the present invention refers to the lipid nanoparticles of the first aspect further comprising a liquid lipid at room temperature. In the context of the present invention, "liquid lipid at room temperature" is understood as that lipid being liquid at room temperature and under 45° C., being able to be saturated or unsaturated. The liquid lipid at room temperature is selected from unsaturated or saturated fatty acid esters, oils, fatty acids and triglycerides having a chain with less than 10 carbon atoms, and their mixtures (for example, triglyceride of caprylic acid and capric acid (Miglyol®), soybean oil, isopropyl myristate, castoroil). In a preferred embodiment, Mygliol® is used as the liquid lipid. In a preferred embodiment, the lipid component of the lipid nanoparticles is a combination of glyceyl palmitostearate (Precirol® ATO5) and triglyceride of caprylic acid and capric acid (Miglyol®). In another variant of this second aspect of the invention, when a liquid lipid at room temperature is incorporated into the nanoparticle, it is in a proportion comprised between 1 and 30% by weight with respect to the total weight of the lipid nanoparticle, preferably between 5 and 15%. In another embodiment, the proportion solid lipid:liquid lipid is between 0.5:10 and 5:10.

In a third aspect of the invention, the present invention refers to a method (method 1 of the invention) for the preparation of the lipid nanoparticle of the first aspect of the invention defined in the paragraphs above, characterized by comprising the following steps:
(i) preparing an aqueous solution comprising a non-ionic surfactant,
(ii) preparing a lipophilic solution comprising a solid lipid at room temperature in an organic solvent,
(iii) adding the aqueous solution (i) to the lipophilic solution (ii), subjecting the resulting mixture to sonication until obtaining an emulsion,
(iv) evaporating the organic solvent of the obtained emulsion in (iii), and
(v) collecting the nanoparticles,
wherein the growth factor is added to the solution (ii).

The lipid nanoparticles obtained with this method 1 are SLN. The first step (i) consists of dissolving the non-ionic surfactant in an aqueous solution, preferably water. The second step (ii) of preparing the lipophilic solution is carried out by means of dissolving the solid lipid at room temperature in an organic solvent, wherein the proportion of the solid lipid is at least 1% by weight with respect to the total weight of the organic solvent. The growth factor, preferably EGF, and more preferably rhEGF, is dissolved together with the lipid in the organic solvent. The choice of the organic solvent depends in a large extent on the lipid component. In a particular embodiment of the invention, the organic solvent is selected from dichloromethane, acetone, chloroform and mixtures thereof, it is more preferably dichloromethane.

Once both solutions are prepared, the aqueous solution (i) is added to the lipophilic solution (ii). The resulting mixture is then subjected to sonication until obtaining an emulsion. Subsequently, the organic solvent is evaporated by means of any method known by a person skilled in the art. In a particular embodiment, the organic solvent evaporation step is carried out by keeping the emulsion under mechanical stirring for at least 60 minutes, preferably at least 120 minutes. After removing the organic solvent, the lipophilic solution solidifies, and a nanoparticle suspension is obtained, which is then filtrated by centrifugation. Finally, collected lipid nanoparticles are washed and resuspended in purified water.

In a fourth aspect of the invention, the present invention refers to a method (method 2 of the invention) for the preparation of the lipid nanoparticle of the second aspect of the invention defined in the paragraphs above, characterized by comprising the following steps:
(i) preparing an aqueous solution comprising a non-ionic surfactant,
(ii) preparing a lipophilic solution comprising a blend of a solid lipid and a liquid lipid melted at a temperature higher than the melting point of the liquid lipid,
(iii) heat the aqueous solution (i) up to the same temperature than the lipophilic solution
(iv) adding the aqueous solution (i) to the lipophilic solution (ii), subjecting the resulting mixture to sonication until obtaining an emulsion,
(v) cooling down the emulsion (iv) at 5° C.±3° C. to allow lipid recrystallization and nanoparticle formation, and
(vi) collecting the nanoparticles,
wherein a growth factor is added to the solution (ii).

The lipid nanoparticles obtained with this method 2 are NLC. The first step (i) consists of dissolving the non-ionic surfactant in an aqueous solution, preferably water. The second step (ii) of preparing the lipophilic solution is carried out by melting a blend of solid lipid and a liquid lipid at a temperature greater than the melting point of the liquid lipid. The growth factor, preferably EGF, and more preferably rhEGF, is dissolved together with the blend of lipid.

Once the aqueous solution (i) is heated up to the temperature that the blend of lipids has been melted, the aqueous solution (i) is added to the lipophilic solution (ii). The resulting mixture is then subjected to sonication until obtaining an emulsion. Subsequently, the emulsion (iv) is cooled down at a temperature of 5° C.±3° C. to allow lipid recrystallization and nanoparticle formation. After lipid recrystallization, a nanoparticle suspension is obtained, which is then filtered by centrifugation. Finally, collected lipid nanoparticles are washed and resuspended in purified water.

A fifth aspect refers to the lipid nanoparticles obtained by the method 1 and the lipid nanoparticles obtained by the method 2.

The lipid nanoparticles of the first, second and fifth aspects of the present invention are characterized by having a mean particle size equal to or less than 1 μm, they preferably have a mean size comprised between 1 nm and 1000 nm, more preferably between 150 nm and 400 nm. The mean size can be measured by standard methods known by the person skilled in the art, and which are described, for example, in the experimental part below (Table 1, Example 2). In addition, the lipid nanoparticles can have a surface charge (measured by means of Z potential), the magnitude can vary from −50 mV to +80 mV (Table 1, Example 2). Moreover, the lipid nanoparticles have an encapsulation efficiency greater than 40%, in particular greater than 70% for SLN and greater than 95% for NLC (Table 1, Example 2).

An important feature of the lipid nanoparticles of the present invention is that they release the loaded growth factor in a sustained released manner. Growth factor-loaded lipid nanoparticles present a release profile characterized by an initial release (burst release) related to the percentage of surface associated protein, followed by a fast release phase from 4 hour to 24 hour and finally, a slower phase from 24 hours to 72 hour is described ending with the release of the total amount of growth factor (Table 3, Example 2).

This sustained release feature provides an important advantage since it enables safer treatments compared with those using free EGF, which require continuous administrations of the growth factor and higher dosage to achieve the same therapeutic effect. In addition, by reducing the dosage, further undesired adverse side effects can be decreased since administration of higher doses of the growth factor is no longer necessary because the encapsulated growth factor is released over the time, in a smaller but more effective dose. Finally, sustained release of the growth factor allows decreasing the number of administrations, increasing patient treatment adherence and consequently, patient's quality of life.

Figure 1:
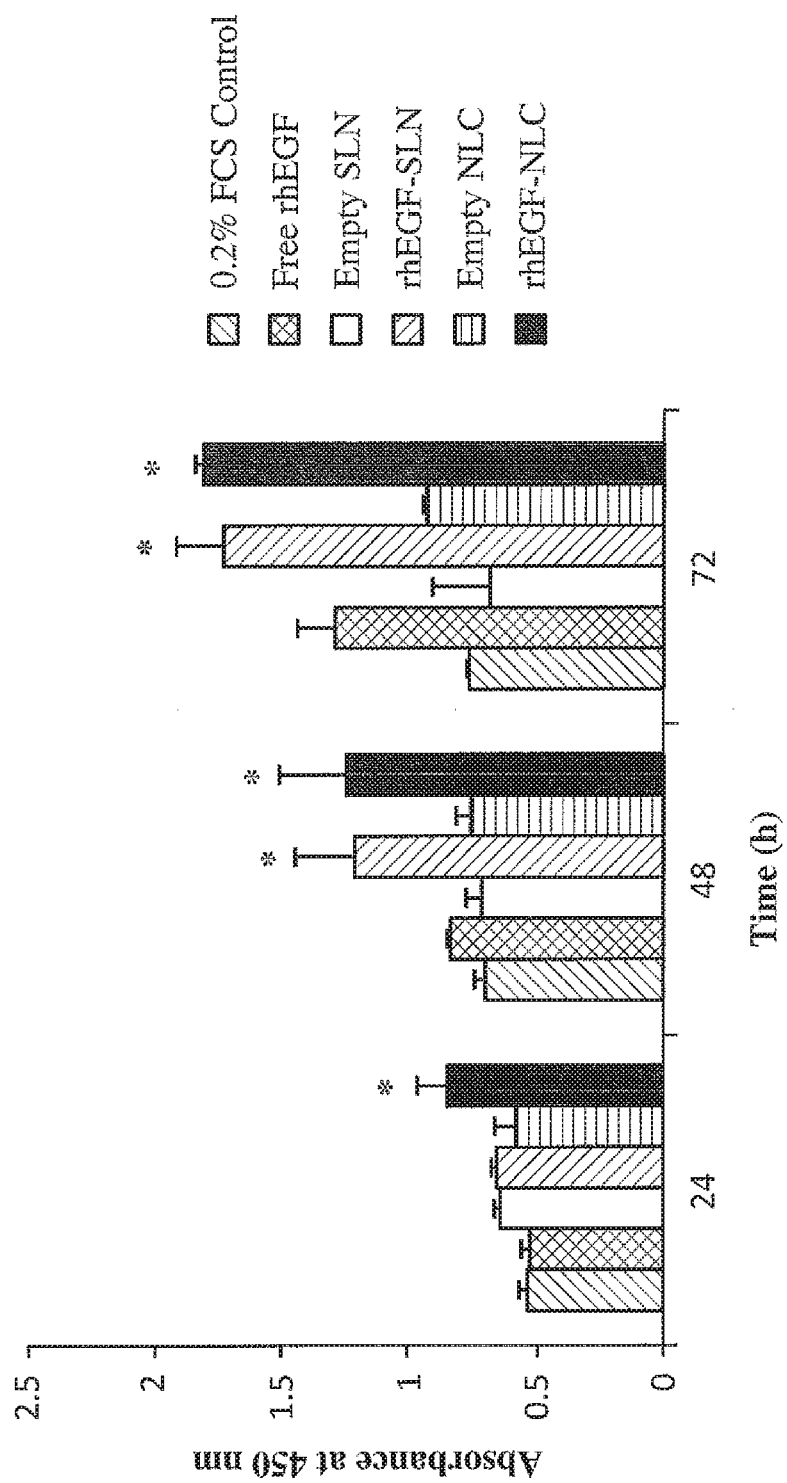
FIG. 1 shows a graphic representation of the in vitro effect of rhEGF-loaded lipid nanoparticles on cell proliferation.

It was surprisingly found by the inventors that the lipid nanoparticles of the present invention, i.e. with EGF-loaded lipid nanoparticles, show an unexpected greater in vitro proliferation rate of fibroblasts than free EGF (Example 3, section 3.1, FIG. 1). Moreover, the lipid nanoparticles of the invention, i.e. EGF-SLN and EGF-NLC, are able to enter into the cell (Example 3, section 3.2, FIG. 2).

Figure 3A:
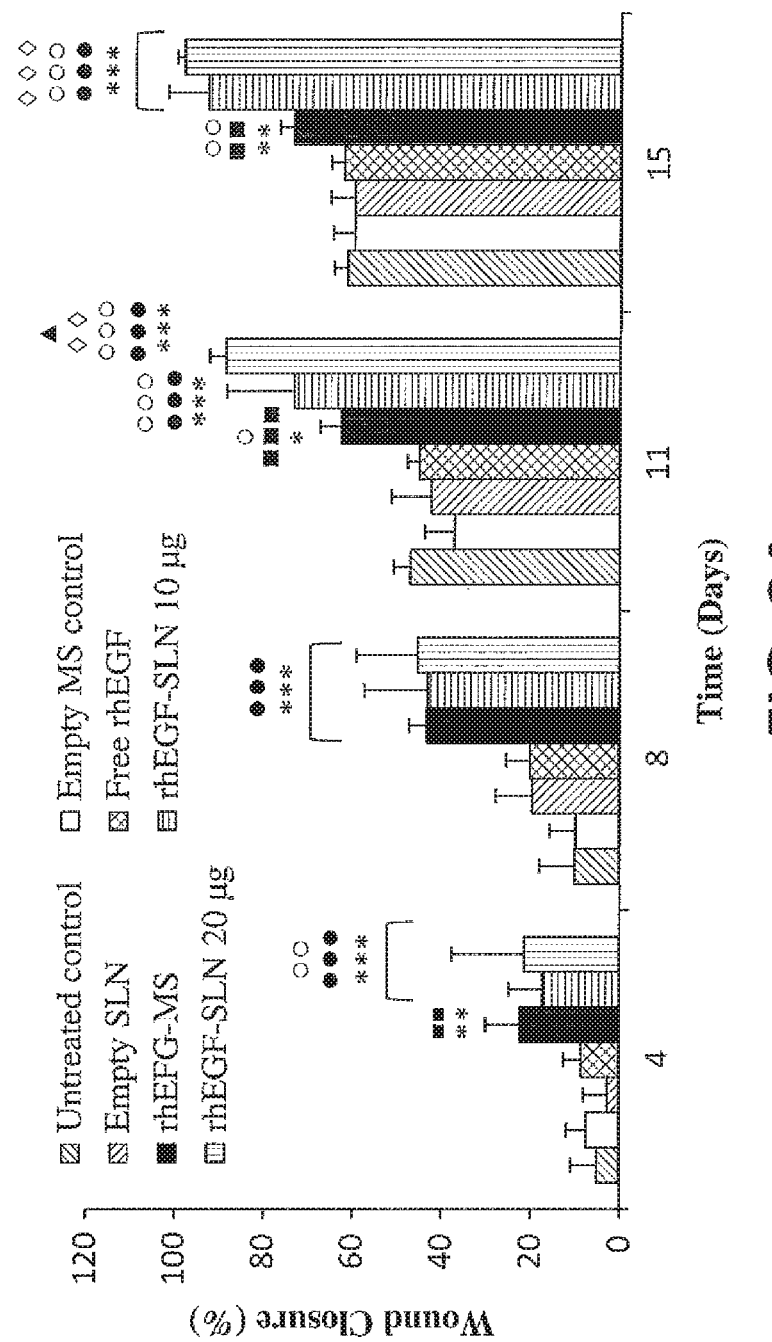
FIG. 3A shows a graphic representation of the in vivo effect of rhEGF-loaded SLN.
Figure 3B:
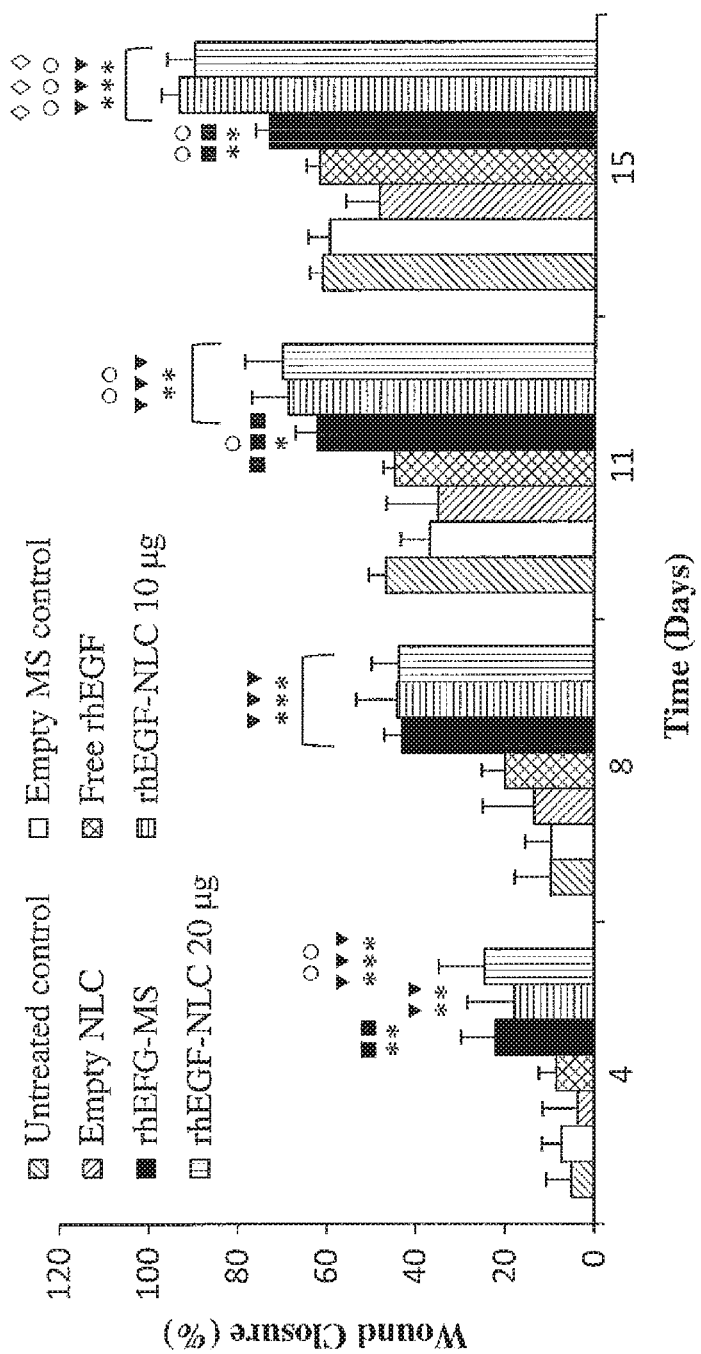
FIG. 3B shows a graphic representation of the in vivo effect of rhEGF-loaded NLC on wound closure.
Figure 3C:
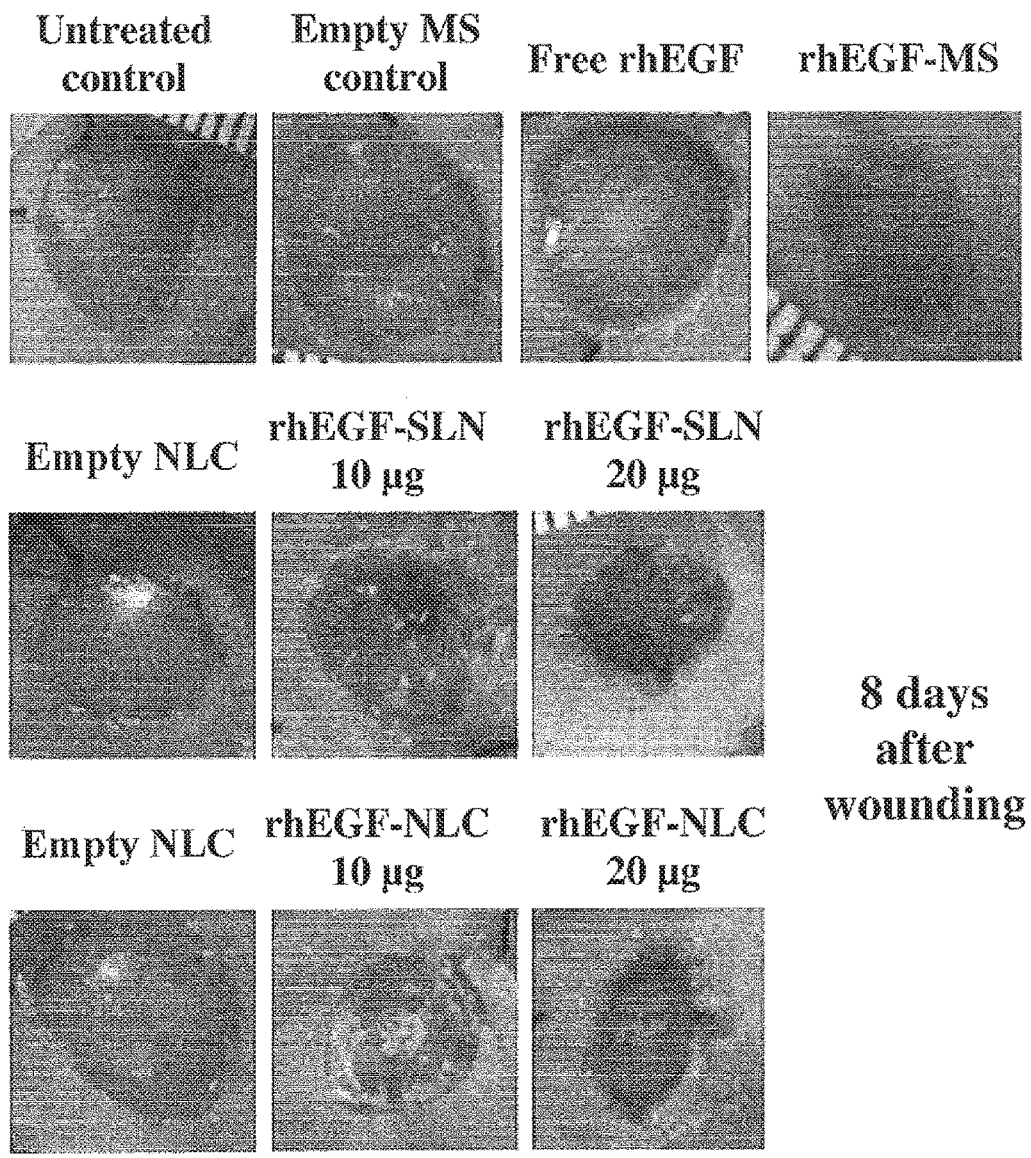
FIG. 3C shows photographs of the wounds in untreated control rats and rats treated with empty SLN, empty NLC, rhEGF-MS, control empty MS, free rhEGF, rhEGF-SLN 20 µg, rhEGF-SLN 10 µg, rhEGF-NLC 20 µg, rhEGF-NLC 10

Interestingly, in vivo studies show that 4 topical administrations of rhEGF-SLN in a dosage of 10 and 20 μg of rhEGF further improve wound healing, in terms of wound closure (FIG. 3. A, C), inflammatory resolution (FIG. 4.A) and re-epithelization process (FIG. 4.B) compared with 300 μg of rhEGF administered in 4 intralesional applications. Moreover, in vivo studies show that 4 topical administrations of rhEGF-NLC in a dosage of 10 and 20 μg of rhEGF further improve wound healing, in terms of wound closure (FIG. 3. B, C), inflammatory resolution (FIG. 4.C) and re-epithelization process (FIG. 4.D) compared with 300 μg of rhEGF administered in 4 intralesional applications. Furthermore, obtained data reveal that the wound healing process was highly improved with 20 or 10 μg of rhEGF encapsulated in SLN and NLC, in terms of wound closure after 8 and 11 days of study, compared with one intralesional dose of 75 μg polylactic-co-glycolic acid (PLGA) microspheres rhEGF-MS. Thus, the use of lipid as a matrix material for a nanoparticle is advantageous over the use of common biodegradable and hydrolytically degradable polymers, such as PLGA, because lipid nanoparticles allow topical administration of the molecule loaded in the lipid nanoparticles.

Additionally, the in vivo studies shown in the Example 6 (FIGS. 8-10) show that local and topical administration of rhEGF-NLC can enhance wound healing not only in terms of speed of wound healing and number of healed wounds (wound closure measurement), but also in terms of healing quality on the basis of the newly formed microvasculature, fibroblast migration, collagen deposition and evolution of the inflammatory response. In addition, these results are very relevant because the animals treated with 20 μg rhEGF-NLC topically administered significantly enhanced healing compared with those lesions treated with 75 μg of free rhEGF intralesionally administered. These data, together with the data from percentage of closed wounds and re-epithelization, demonstrate that rhEGF nanoencapsulation into rhEGF-NLC permits topical administration, and allows dose reduction because encapsulation prevents the growth factor degradation in the wound site.

Interestingly, EGF-SLN and EGF-NLC show improved skin penetration capacity compared with paraffin cream (Example 3, section 3.4, FIG. 5). This is an important advantage because it allows the topical administration of the molecule loaded in the lipid nanoparticles.

Thus, a sixth aspect of the present invention refers to a pharmaceutical composition comprising the lipid nanoparticle of the invention defined in the first, second and fifth aspect of the invention, as described in any of the paragraphs above, and a pharmaceutical carrier. In a preferred embodiment of this aspect, the pharmaceutical composition is topically administered. It can be administered in the form of a gel, cream, ointment, dressing or as a patch. Thus, in a particular embodiment, the pharmaceutical composition further comprises collagen, hyaluronic acid, aloe vera, fibrin, Carbopol® polymers and cellulose derivates.

Moreover, a seventh aspect of the present invention refers to the lipid nanoparticle defined in the first, second and fifth aspect of the invention as described in any of the paragraphs above for its use as a medicament. Moreover, in an eight aspect, the invention refers to the pharmaceutical composition defined in the sixth aspect for its use as a medicament.

Taking into account the in vivo results described above, another aspect of the invention, ninth aspect of the invention, refers to the lipid nanoparticle defined in the first, second and fifth aspect of the invention described in any of the paragraphs above, for its use in promoting wound healing in a subject. Preferably, it refers to EGF-loaded SLN for its use in promoting wound healing in a subject, and to EGF-loaded NLC for its use in promoting wound healing in a subject. Moreover, in a tenth aspect, the invention refers to the pharmaceutical composition defined in the sixth aspect for its use in promoting wound healing in a subject. The term "subject" as used herein refers to any vertebrate animal, preferably a mammal, and more preferably a human. In the context of the present invention, wound refers to chronic wounds, difficult-to-heal wounds, ischemic wounds and burns. In a particular embodiment, the wound is selected from the group comprising chronic wounds, isquemic wounds, burns and combinations thereof. Preferred chronic wounds are selected from the group consisting of diabetic foot ulcers, pressure ulcers, vascular ulcers and mixtures thereof.

In the context of the present invention, chronic wounds are defined as wounds that have failed to proceed through an orderly and timely reparative process to restore anatomic and functional integrity over a period of three months. All wound types have the potential to become chronic and, as such, chronic wounds are traditionally divided etiologically into three categories: pressure, diabetic and vascular ulcers (venous and arterial ulcers). A pressure ulcer is defined as an area of localised damage to the skin and/or underlying tissue, usually over a bony prominence, as a result of pressure or shear, and/or a combination of these. Diabetic foot ulcers are one of the most feared complications of diabetes due to the high consequences on the patient quality of life, and appear as a result of various factors, such as mechanical changes in conformation of the bony architecture of the foot, peripheral neuropathy (damaged nerves) and peripheral vascular disease (block arteries), all of which occurring with higher frequency and intensity in the diabetic population. Vascular ulcers are usually localised on lower limbs. The great majority of vascular ulcers are chronic or recurrent. They cause considerable morbidity among patients with peripheral vascular disease. Arterial or ischemic wounds are caused by poor perfusion to the lower extremities. Ischemia limits the supply of nutrients and oxygen, killing the tissues and causing in the area the formation of an open wound. Reduced blood flow to the wound site severely impairs the healing response, causing a chronic wound that can lead to gangrene, and thus, to amputation. Finally, difficult-to-heal wounds are characterized by the chronic persistence of inflammatory cells, disordered synthesis and remodelling of the extracellular matrix, and lack of re-epithelialization; and burns are damage to the skin caused by the effect of heat, fire, radiation, sunlight, electricity or chemicals.

It was surprisingly found by the inventors that the combination of EGF and the cathelicidin antimicrobial peptide LL37, show an unexpected greater cell proliferation than free EGF and free LL37, respectively (Example 4, FIG. 7). The LL37 peptide corresponds to the C-terminal fragment of the human cathelicidin anti-microbial protein, hCAP18, which is a component of the innate immune system and has broad anti-microbial activity (Heilborn et al., 2003, *The cathelicidin antimicrobial peptide LL37 is involved in re-epithelization of human skin wounds and is lacking in chronic ulcer epithelium.* J Invest Dermatol 120(3): 379-389). Thus, a eleventh aspect of the present invention refers to a composition (composition of the invention) comprising lipid nanoparticles according to the first, second and fifth aspect of the present invention and lipid nanoparticles comprising at least one solid lipid at room temperature, at least one non-ionic surfactant and the LL37 peptide. In a particular embodiment of this aspect, the composition comprises EGF-loaded NLC and LL37-loaded NLC. In another particular embodiment, the composition comprises EGF-loaded SLN and LL37-loaded SLN. In another particular embodiment of this aspect, in the composition of the invention the ratio of growth factor-loaded, preferably EGF-loaded, lipid nanoparticles and LL37-loaded lipid nanoparticles is between 1:17 and 1:34. In another particular embodiment, the composition comprises 15 ng/ml of EGF-loaded lipid nanoparticles and 0.25 to 5 µg/ml of LL37-loaded lipid nanoparticles.

A twelfth aspect of the present invention is a pharmaceutical composition comprising the composition according to the eleventh aspect of the invention described in the last paragraph, and a pharmaceutical carrier. In a preferred embodiment of this aspect, the pharmaceutical composition is topically administered. Thus, in a particular embodiment, the pharmaceutical composition further comprises collagen, hyaluronic acid, aloe vera, fibrin, Carbopol® polymers and cellulose derivates.

Furthermore, a thirteenth aspect of the present invention refers to the pharmaceutical composition of the twelfth aspect, for its use as a medicament.

A fourteenth aspect of the present invention, refers to the pharmaceutical composition defined in the twelfth aspect, for its use in promoting wound healing in a subject.

A fifteenth aspect of the present invention, refers to a lipid nanoparticle comprising at least one solid lipid at room temperature, at least one non-ionic surfactant and the LL37 peptide. The particular embodiments described in the first aspect of the present invention are applicable to the LL37-loaded lipid nanoparticles of the fifteenth aspect, substituting the growth factor or EGF by the LL37 peptide.

A sixteenth aspect of the present invention, refers to the lipid nanoparticle of the fifteenth aspect further comprising a liquid lipid at room temperature. The particular embodiments described in the second aspect of the present invention are applicable to the LL37-loaded lipid nanoparticles of this aspect substituting the growth factor or EGF by the LL37 peptide.

A seventeenth aspect of the present invention, refers to a method (method 3 hereinafter) for the preparation of lipid nanoparticles according to the fifteenth aspect of the present invention, which is characterized by the same steps of the method 1 described in the third aspect of the present invention, but wherein the LL37 peptide is added to the lipophilic solution (ii), instead of the growth factor. The particular embodiments described for the method 1 described in the third aspect of the present invention are applicable to method 3, substituting the growth factor or EGF by the LL37 peptide.

An eighteenth aspect of the present invention, refers to a method (method 4 hereinafter) for the preparation of lipid nanoparticles according to the sixteenth aspect of the present invention, which is characterized by the same steps of the method 2 described in the fourth aspect of the present invention, but wherein the LL37 peptide is added to the lipophilic solution (ii), instead of the growth factor.

A nineteenth aspect of the present invention refers to the lipid nanoparticles obtainable by the method 3 and the lipid nanoparticles obtainable by the method 4, described in aspects seventeenth and eighteenth, respectively.

Regarding LL37, this peptide can be synthesized using an automatic peptide synthesizer and standard methods for peptide syntheses. Moreover, it can be obtained commercially, for example from Sigma-Aldrich. LL37 has the aminoacid sequence SEQ ID NO 1 (LLGDFFRKSKEKIG-KEFKRIVQRIKDFLRNLVPRTES).

An important feature of the LL37-loaded lipid nanoparticles of the present invention is that they release the loaded LL37 in a sustained released manner. LL37-loaded lipid nanoparticles present a release profile characterized by an initial release (burst release) related to the percentage of surface associated peptide, followed by a fast release phase from 4 hours to 24 hours and finally, a slower phase from 24 hours to 72 hours is described ending with the release of the total amount of LL37 (Table 4, Example 2).

Surprisingly, the inventors show that the LL37-loaded lipid nanoparticles, have an unexpected greater in vitro proliferation rate of fibroblasts than free LL37 (Example 3, section 3.3, FIG. 6). Thus, a twentieth aspect of the present invention refers to the LL37-loaded lipid nanoparticles of the fifteenth, sixteenth and nineteenth aspects of the present invention, for their use as a medicament.

A twenty first aspect of the present invention, refers to the LL37-loaded lipid nanoparticles of the fifteenth, sixteenth and nineteenth aspects of the present invention, for its use in promoting wound healing in a subject.

A twenty second aspect of the present invention refers to a pharmaceutical composition comprising the LL37-loaded lipid nanoparticles of the fifteenth, sixteenth and nineteenth aspects of the present invention, and a pharmaceutical acceptable carried. In a preferred embodiment of this aspect, the pharmaceutical composition is topically administered. Thus, in a particular embodiment, the pharmaceutical composition further comprises collagen, hyaluronic acid, aloe vera, fibrin, Carbopol® polymers and cellulose derivates.

The present invention also refers, in a twenty third aspect, to the pharmaceutical composition of the twenty second aspect for its use as a medicament.

A twenty fourth aspect of the present invention refers to the pharmaceutical composition defined in the twenty second aspect, for its use in promoting wound healing Finally, a twenty fifth aspect of the present invention refers to a kit comprising any one of the lipid nanoparticles described in the first, second, fifth, fifteenth, sixteenth and nineteenth aspect of the present invention, or mixtures thereof. Additionally, it refers to a kit comprising a pharmaceutical composition according to any of the pharmaceutical compositions described in the sixth, twelfth and twenty second aspect of the invention.

The examples below serve to further illustrate the invention, and to provide those of ordinary skill in the art with a complete disclosure and description of how the lipid nanoparticles herein are prepared and evaluated, and are not intended to limit the scope of the invention. In the examples, unless expressly stated otherwise, amounts and percentages are by weight, temperature is in degree Celsius or is at ambient temperature, and pressure is at or near atmospheric.

EXAMPLES

Example 1: Lipid Nanoparticle Preparation

SLN and NLCs were prepared by the emulsification-ultrasonication based method (Muller et al., 2002; Che et al., 2010 (*Effects of lipophilic emulsifiers on the oral administration of lovastatin from nanostructured lipid carriers: Physicochemical characterization and pharmacokinetics*. European Journal of Pharmaceutics and Biopharmaceutics 74, 474-482).

In case of rhEGF-loaded SLN, 10 ml of 1% (v/v) Tween 80 aqueous solution was added to a 2 ml of a dichloromethane solution containing 0.1% (w/v) commercial rhEGF and 10% (w/w) Precirol® ATO 5. Immediately after, the mixture was emulsified for 30 seconds at 50 W (Branson® 250 sonifier, CT, USA). This step produced an o/w emulsion which was then stirred for 2 hours to extract the organic solvent and to obtain particle hardening. The SLN were then collected by centrifugation at 2500 rpm for 10 minutes using a centrifugal filter unit with 100 kDa on pore size (Amicon® Ultra, Millipore, Spain), and washed three times with miliQ water. Finally, trehalose was added as cryoprotectant in an aqueous solution of 15% respect to Precirol® ATO 5.

Concerning the preparation of rhEGF-loaded NLC, a warm aqueous solution of 0.67% (w/v) Poloxamer and 1.33% (w/v) Tween 80, heated at 40° C. for 1 minute, was poured into a 200 mg of melted Precirol® ATO 5 based mixture containing 2 mg of commercial rhEGF and 20 mg of Miglyol, also heated at 40° C. for 1 minute. The resulting blend was then emulsified for 15 seconds at 50 W (Branson® 250 sonifier, CT, USA) and stored for 12 hours at 4° C., recrystallising the lipid, to allow NLC formation. Finally, particles were collected, washed and lyophilised as previously described. The target loading of rhEGF both in SLN and NLC was 1% (w/w).

The LL37-loaded SLN and LL37-loaded NLC were prepared as described for the rhEGF-loaded SLN and rhEGF-loaded NLC, respectively, but using synthetic (Sigma-Aldrich 94261) or recombinant LL37 peptide, instead of rhEGF.

Example 2.—Lipid Nanoparticle Characterization 2.1.—The mean size (z-average) and polydispersity index (PI) were measured by photon correlation spectroscopy. Each assay was performed in triplicate before and after nanoparticle lyophilization. Zeta potential ($\zeta$) was determined through Doppler velocimetry (LDV). All the measurements described above were assessed using a Malvern® Zetasizer 3000 instrument (Malvern Instruments, Worcestershire, UK). Surface appearance and sphere morphology was determined through scanning electron microscopy (SEM; Jeol® JSM-35 CF) and transmission electron microscopy (TEM).

2.2.—The encapsulation efficiency (EE) was calculated indirectly measuring free rhEGF and free LL37 (non-encapsulated) removed by the filtration/centrifugation technique used to collect the SLN and NLC. Each sample was diluted 1:10000 with Dulbecco's phosphate buffered saline (DPBS) solution containing 0.05% (v/v), Tween 20 and 0.1% (w/v) Bovine Serum Albumin (BSA). The amount of free rhEGF and free LL37 was estimated using a commercially available Sandwich Enzyme-Linked Immunosorbent assay kit for human EGF (human EGF ELISA development kit, Peprotech) and for human LL37 (Human LL-37 ELISA development kit, Hycult biotech), following manufacturer's instructions. Encapsulation efficiency (EE) was assessed applying the following equation:

$$EE\ (\%) = \frac{\text{Total amount of } rhEGF\ (LL37) - \text{Free } rhEGF\ (LL37)}{\text{Total amount of } rhEGF\ (LL37)} \times 100$$

All tests were performed in triplicate, and results are reported as the means±S.D. of these assays.

TABLE 1 rhEGF-loaded SLN and NLC characterization:

| Formulation | Before liophylization | | After liophylization | | Zeta potential (mV) | EE (%) |
| --- | --- | --- | --- | --- | --- | --- |
| | Size (nm) | PDI | Size (nm) | PDI | | |
| SLN | 226.1 ± 0.8 | 0.28 | 310.9 ± 15.8 | 0.30 | −33.8 ± 0.3 | 73.9 ± 2.2 |
| NLC | 241.5 ± 23.3 | 0.38 | 353.6 ± 4.53 | 0.37 | −34.6 ± 0.2 | 95.7 ± 4.7 |

TABLE 2

LL37-loaded SLN and NLC characterization:

| Formulation | Before liophylization | | After liophylization | | Zeta potential | |
|---|---|---|---|---|---|---|
| | Size (nm) | PDI | Size (nm) | PDI | (mV) | EE (%) |
| SLN | 251.53 ± 7.79 | 0.35 ± 0.02 | 340.27 ± 2.42 | 0.25 ± 0.01 | −33.97 ± 0.57 | 70.67 ± 0.22 |
| NLC | 225.4 ± 1.26 | 0.35 ± 0.07 | 320.90 ± 3.72 | 0.37 ± 0.01 | −33.47 ± 1.78 | 97.52 ± 0.75 |

As shown in Tables 1 and 2, the PDI values were less than 0.5 in all the formulations before and after freeze-drying, confirming the homogeneous size distribution of the formulations in all cases. Reconstitution of dry particles for size measurements did not present any inconvenience, suggesting the absence of particle fusion or aggregation, despite the increase in size. Regarding to the zeta potential, both formulations presented similar surface charge, of approximately −34 mV. In addition, ELISA assays demonstrated that NLC EE was slightly higher than SLN EE.

In both formulations the surface of nanoparticles was smooth and pore free. In contrast, both SEM images and TEM images suggested that SLN were more regular in size than NLC (data not shown).

2.3.—In Vitro Release Studies

The release study was conducted by incubating 32 mg and 23 mg of SLN or NLC (corresponding to ~200 µg of rhEGF or LL-37) in 2 ml of 0.02 M phosphate-buffered saline (PBS) for three days. At selected intervals, the release medium was removed by filtration/centrifugation and replaced by the same quantity of PBS. The amount of rhEGF and LL37 was assayed by ELISA using the protocol described in section 2.2.

TABLE 3

Cumulative percentage of rhEGF released over time

| Time | rhEGF cumulative release from SLN | rhEGF cumulative release from NLC |
|---|---|---|
| 30 minutes | 25.15 ± 3.19 | 26.88 ± 3.19 |
| 4 hours | 38.50 ± 10.09 | 44.79 ± 5.02 |
| 8 hours | 57.11 ± 13.44 | 61.31 ± 5.04 |
| 24 hours | 71.20 ± 17.36 | 75.87 ± 5.88 |
| 48 hours | 88.27 ± 23.80 | 86.10 ± 6.23 |
| 72 hours | 102.24 ± 24.59 | 98.95 ± 8.02 |

TABLE 4

Cumulative percentage of LL37 released over time

| Time | LL37 cumulative release from SLN | LL37 cumulative release from NLC |
|---|---|---|
| 30 minutes | 27.60 ± 2.96 | 31.21 ± 10.56 |
| 4 hours | 45.19 ± 6.82 | 52.14 ± 4.57 |
| 8 hours | 55.87 ± 4.31 | 65.18 ± 6.21 |
| 24 hours | 62.51 ± 21.22 | 74.93 ± 10.20 |
| 48 hours | 89.00 ± 12.41 | 93.81 ± 5.25 |
| 72 hours | 100.76 ± 19.20 | 105.70 ± 10.25 |

The in vitro rhEGF and LL37 release profiles displayed in Table 3 and Table 4, respectively, show that both formulations presented a similar release behaviour. Firstly an initial release (burst release) related to the percentage of surface associated protein or peptide, followed by a fast release phase from 4 hours to 24 hours and finally, a slower phase from 24 hours to 72 hours is described ending with the release of the total amount of rhEGF and LL37.

Example 3.—Cell Proliferation, Cellular Uptake and Skin Penetration of Nanoparticles 3.1.—Effect of rhEGF-Loaded Nanoparticles on Cell Proliferation 24-well plate was used for the proliferation assay. 35000 Balb/C 3T3 fibroblast resuspended in 1 ml of completed culture medium (DMEM supplemented with 10% FCS) were seeded in each well. After 8 hours of incubation, the medium was replaced by 1 ml of 0.2% FCS supplemented DMEM and cells were incubated overnight. Then, medium was replaced by 1 ml of: (i) 0.2% FCS-supplemented DMEM, (ii) 15 ng/ml of free rhEGF in 0.2% FCS-supplemented DMEM, (iii) empty SLN in 0.2% FCS-supplemented DMEM, (iv) 15 ng/ml of rhEGF-loaded SLN (rhEGF-SLN) in 0.2% FCS-supplemented DMEM, (v) empty NLC in 0.2% FCS-supplemented DMEM and (vi) 15 ng/ml of rhEGF-loaded NLC (rhEGF-NLC) in 0.2% FCS-supplemented DMEM.

The cells were cultured under the same conditions for 24 hours, 48 hours and 72 hours. The experiments were performed in triplicate. After the different incubation intervals, 100 µl of CCK-8 (Sigma-Aldrich, Saint Louise, USA) was added to each well (Zhou, Y., Qian, M., Liang, Y., Liu, Y., Yang, X., Jiang, T., Wang, Y., 2011. *Effects of Leukemia Inhibitory Factor on Proliferation and Odontoblastic Differentiation of Human Dental Pulp Cells.* J. Endod. 37, 819-824). After 4 hours of incubation, absorbance was read at 450 nm and at 650 nm as the reference wavelength. The absorbance was directly proportional to the number of living cells in culture.

The proliferation assay carried out in Balb/c 3T3 cells demonstrated the mitogenic effect of rhEGF. FIG. 1 shows greater cell proliferation in groups treated with rhEFG (rhEGF-NLC, rhEGF-SLN and free rhEGF) than control groups, after 48 hours and 72 hours. Strikingly, rhEGF encapsulated into lipid nanoparticles (either SLN or NLC) showed a greater increase in the mitogenic effect of Balb/C 3T3 fibroblast than free rhEGF.

3.2.—The Effect of LL37-Loaded Nanoparticles on Cell Proliferation

The experiment was carried out as described in section 3.1 but with HUVEC cells (Human Umbilical Vein Endothelial Cells). The tested groups were the following: (i) 0.2% FCS-supplemented DMEM, (ii) 0.5 and 0.1 µg/ml of free LL37 in 0.2% FCS-supplemented DMEM, (iii) empty SLN in 0.2% FCS-supplemented DMEM, (iv) 0.5 and 0.1 µg/ml of LL37-loaded SLN (LL37-SLN) in 0.2% FCS-supplemented DMEM, (v) empty NLC in 0.2% FCS-supplemented DMEM, (vi) 0.5 and 0.1 µg/ml of LL37-loaded NLC (LL37-NLC) in 0.2% FCS-supplemented DMEM and (vii) 10% DMSO as negative control.

The proliferation assay carried out on HUVEC cells demonstrated the mitogenic effect of LL37. FIG. 6 shows greater cell proliferation in groups treated with LL37 (LL37-NLC, LL37-SLN and free LL37) than control groups for both doses after 48 hours.

3.3.—Cellular Uptake of NileRed-SLN and NileRed—NLC Formulations

50000 Balb/C 3T3 fibroblast and 100000 HaCaT keratynocites were cultured separately on coverslips in complete culture medium for 24 hours. The medium was then replaced with 1 ml of assay medium. The following groups were tested: (i) 25 µg of NileRed-SLN in completed DMEM and (ii) 25 µg of NileRed-NLC in completed DMEM. After 1 hour incubation, cells were washed and fixed. Nuclei were then stained with DAPI (500 ng/ml) and coverslips were mounted into the slides for examination in a fluorescence microscope.

Figure 2:
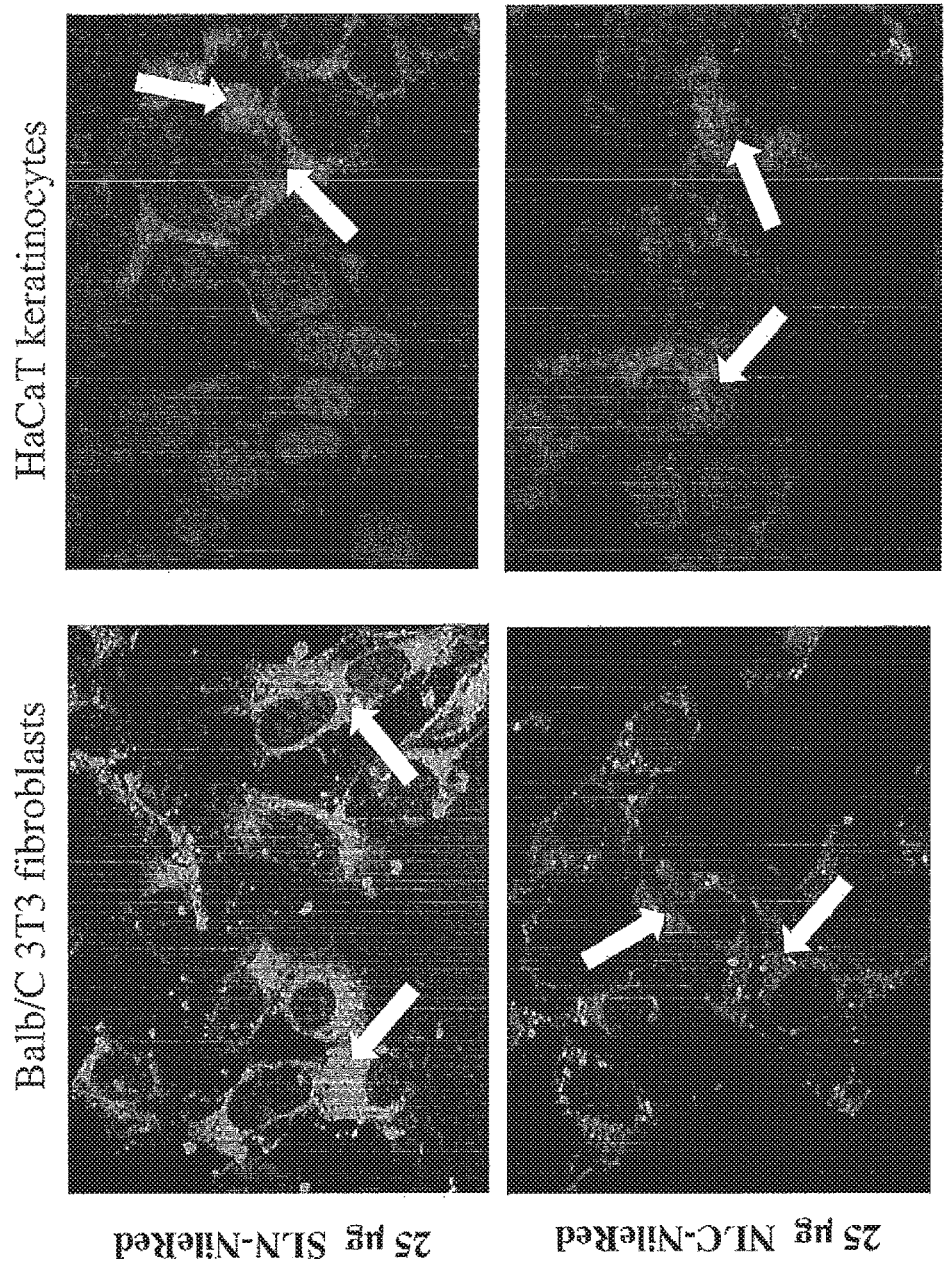
FIG. 2 shows a micrograph of the cellular uptake of NileRed-SLN and NileRed-NLC formulations.

The results obtained from the cellular uptake study are presented in FIG. 2. The cell cytoplasm turns red (white arrows in FIG. 2) due to the internalization of the SLN and NLC. The figure shows the capability of the SLN-NileRed and NLC-NileRed to enter into the cell. No differences were observed between the uptake capability of SLN and NLC.

3.4.—Coetaneous Uptake of SLN and NLC Formulations

The experiment was carried out as described by Küchler et al., 2009 (*Nanoparticles for skin penetration enhancement—A comparison of dendritic core-multishell-nanotransporter and solid lipid nanoparticles*. Eur J Pharm Biopharm.; 71:243-250). The skin of the same animal was used for treated and control experiments. The groups assayed were (n=3) (i) SLN-NileRed, (ii) NLC-NileRed and (iii) Nile red loaded paraffin cream used as a reference. All preparations had Nile red at identical concentration of 0.004%. Skin was maintained for 24 hours at 32° C. Skin was then washed with PBS, dried and cut into vertical slices (bottom to surface) of 20 µm thickness using a freeze microtome Frigocut 2800 N, Leica, Bensheim, Germany. Slices were stored at −20° C. and analysed within 24 hours, subjecting then to normal light and fluorescence light.

For all experiments, the corrected arbitrary pixel brightness values ABU obtained from dye uptake were related to uptake data from Nile red loaded paraffin cream. The resulting parameter called penetration enhancing effect (PEE) was calculated for all skin layers. The value of the paraffin cream was 1 by definition (Lombardi Borgia, S., Regehly, M., Sivaramakrishnan, R., Mehnert, W., Korting, H. C., Danker, K., Roder, B., Kramer, K. D., Schafer-Korting, M., 2005. *Lipid nanoparticles for skin penetration enhancement-correlation to drug localization within the particle matrix as determined by fluorescence and parelectric spectroscopy*. J. Control. Release 110, 151-163).

Penetration enhancing effect (PEE) values, estimated from the corrected arbitrary pixel brightness (ABU) values of the skin sections are presented in FIG. 5. PEE values showed that dye penetration of SLN-NileRed and NLC-NileRed exceed those found with the paraffin cream in all the skin slides. PEE values for SLN-NileRed and NLC-NileRed increased fourfold in the stratum corneum (4.74 and 4.62 respectively) and about twofold in epidermis (2.09 and 2.03 respectively). A minor, yet still often significant enhanced penetration was also observed in the dermis (1.29 and 1.32 respectively). In short, the ABU and PEE values over 1 demonstrate an improved skin penetration capacity of SLN and NLC compared with the paraffin cream. Furthermore, data also reflect the capability of these nanoparticles to deliver Nile Red to the skin and therefore rhEGF and LL37.

Example 4.—In Vitro Proliferation of rhEGF/LL37/Combination rhEGF and LL37

The experiment was carried out as described in section 3.1. The synergy effect of LL37 and rhEGF was tested in Balb/C fibroblast and HaCat keratynocites. 24-well plate was used for the proliferation assay. 35000 Balb/C 3T3 fibroblast resuspended in 1 ml of completed culture medium (DMEM supplemented with 10% FCS) were seeded in each well. After 8 hours of incubation, the medium was replaced by 1 ml of 0.2% FCS supplemented DMEM and cells were incubated overnight. Medium was then replaced by 1 ml of: (i) 0.2% FCS-supplemented DMEM, (ii) 15 ng/ml of free rhEGF, (iii) 5, 0.5 and 0.25 µg/ml of LL37, (iv) 15 ng/ml of rhEGF and 5, 0.5 and 0.25 µg/ml of LL37. Cells were cultured at 37° C. and 5% $CO_2$ atmosphere for 24 hours, 48 hours and 72 hours.

The proliferation assay carried out in HaCaT (human queratinocytes) and Balb/C fibroblast demonstrated the after 48 hours, 10 and 50 ng/ml LL37 and 15 ng/ml rhEGF higher enhanced mitosis than free rhEGF alone (FIG. 7).

Example 5.—In Vivo Wound Healing with rhEGF-Loaded SLN and rhEGF-Loaded NLC

In vivo wound healing efficacy of rhEGF-loaded SLN and rhEGF-loaded NLC was tested against two different rhEGF formulations. (i) 75 µg of lyophilised rhEGF (similar to commercialised Heberprot®) and (ii) 75 µg of rhEGF encapsulated in 1% (w/w) loaded polymeric microspheres (rhEGF-MS 75 µg) prepared in our laboratory by the combination with alginate and polylactic-co-glycolic acid (PLGA) using double-emulsion method as described in the European patent application EP12382476. Briefly, 2 ml of dichloromethane:acetone (3:1) solution containing 5% (w/v) of PLGA (Resomer RG503) was emulsified by sonication for 15 seconds at 50 W with 0.2 ml of an internal aqueous phase (in miliQ water) containing 0.05% (w/v) rhEGF, 2.5% mg (w/v) of Human Serum Albumin (HSA), 0.25% (w/v) of polyethylene glycol 400 (PEG400) and 2.5% (w/v) sodium alginate MVG (Pronova UP, NovaMatrix FMC BioPolymer, Sandvika, Norway). The resulting emulsion ($w_1$/o) was poured into 15 ml aqueous solution containing 5% polyvinyl alcohol (PVA) and 5% NaCl, and emulsified using a paddle stirrer during 60 seconds to obtain the double emulsion ($w_1$/o/$w_2$). Finally, 400 ml of an aqueous solution of 5% NaCl and 0.6 mM of calcium chloride was added and stirred for 30 minutes. The microspheres were then collected by filtration and lyophilized.

5.1.—Animals

Eighty 8-week-old male db/db mice were used. Genetically diabetic db/db mice (BKS.Cg-m+/+ $Lepr^{db}$/J) were obtained from Javier Laboratories (Saint Berthevin Cedex). All procedures were performed according to protocols approved by the Institutional Animal Care and Use Committee of the University of the Basque Country.

5.2.—Experimental Procedure

The experiments were performed by adapting the procedure used by Michaels et al.

(2007) (db/db *mice exhibit severe wound-healing impairments compared with other murine diabetic* strains *in a silicone-splinted excisional wound model*. Wound Repair and Regeneration 15, 665-670). Animals were divided into the following 10 groups (n=8): (i) untreated control, (ii) 75 µg of free rhEGF, (iii) empty MS, (iv) empty SLN, (v) empty NLC, (vi) rhEGF-MS 75 µg, (vii) rhEGF-SLN 10 µg, (viii) rhEGF-SLN 20 µg (ix) rhEGF-NLC 10 µg and (x) rhEGF-NLC 20 µg.

It is also remarkably that multiple free rhEGF administrations showed fewer differences among all the control groups than those presented by the nanoformulated rh-EGF groups.

TABLE 5

Wound healing

| Experimental groups | 4$^{th}$ day (%) | 7$^{th}$ day (%) | 11$^{th}$ day (%) | 14$^{th}$ day (%) |
|---|---|---|---|---|
| Untreated Control | 5.04 ± 5.71 | 9.86 ± 7.94 | 46.76 ± 3.77 | 61.12 ± 2.85 |
| Empty MS | 7.35 ± 4.36 | 9.63 ± 5.85 | 36.94 ± 6.46 | 59.55 ± 4.82 |
| Empty SLN | 2.66 ± 5.25 | 19.50 ± 8.07 | 42.18 ± 8.82 | 59.53 ± 5.37 |
| Empty NLC | 3.57 ± 7.95 | 13.51 ± 11.43 | 35.14 ± 11.54 | 48.38 ± 7.57 |
| Free rhEGF | 8.42 ± 3.96 | 19.94 ± 5.21 | 44.80 ± 2.64 | 61.83 ± 2.99 |
| rhEGF-MS 75 µg | 22.10 ± 7.73 | 43.12 ± 3.97 | 62.31 ± 4.88 | 73.16 ± 3.24 |
| rhEGF-SLN 10 µg | 17.03 ± 7.61 | 42.70 ± 14.40 | 71.05 ± 18.53 | 92.33 ± 9.05 |
| rhEGF-SLN 20 µg | 21.08 ± 16.29 | 45.02 ± 13.84 | 88.40 ± 3.53 | 97.75 ± 1.67 |
| rhEGF-NLC 10 µg | 17.88 ± 10.55 | 44.28 ± 9.16 | 68.80 ± 8.15 | 93.64 ± 3.95 |
| rhEGF-NLC 20 µg | 24.64 ± 10.17 | 43.81 ± 6.20 | 70.10 ± 8.47 | 90.11 ± 6.17 |

Nanoparticles previously resuspended in 20 µl of vehicle (0.5% carboxymethylcellulose in 0.9% saline) were administered topically twice a week with a micropipette and were allowed to spread over the wound bed. Free rhEGF resuspended in 0.5 ml of vehicle was intralesionally administered twice a week by deepening the needle downward into the wound. rhEGF-MS 75 µg also resuspended in 0.5 ml of vehicle was intralesionally administered once in the day of wound induction.

5.3.—Evaluation of Wound Healing

The effectiveness of treatments in improving wound healing was evaluated by measuring the wound area (cm$^2$) on the day of surgery and on days 4, 8, 11 and 15 after wound induction (FIG. 3B), using a digital camera (Lumix FS16, Panasonic®, Spain) and an image analysis program (ImageJ®, Biophotonics Facility, University of McMaster, Canada). The wound closure was expressed as the percentage area of the initial wound size.

All experimental groups (rhEGF-SLN 20 and 10 µg, rhEGF-NLC 20 and 10 µg and rhEGF-MS 75 µg) presented greater wound area reduction from day 4 (FIG. 3A) compared with their control groups (for rhEGF-SLN groups their controls are free rhEGF, empty SLN and untreated control; for rhEGF-NLC groups their controls are free rhEGF, empty NLC and untreated control; and for rhEGF-MS 75 µg its controls are free rhEGF, empty MS and untreated control). No statistical differences were found between both lipid nanoparticles formulations (rhEGF-SLN and rhEGF-NLC), in contrast wound contraction became significantly greater than rhEGF-MS 75 µg and free rhEGF (p<0.001). Regarding control groups, rhEGF-MS 75 µg also showed statistically significant wound closure. By day 8, wound contraction reached the greatest difference among all experimental groups and their controls. Again, no differences were found among rhEGF-SLN, rhEGF-NLC and rhEGF-MS 75 µg formulations. Interestingly, 11 days after wounding, the animals treated with rhEGF-SLN 20 µg showed significantly further wound reduction than the other experimental groups (p<0.05 for rhEGF-SLN 10 µg, rhEGF-NLC 20 and 10 µg and p<0.001 for rhEGF-MS 75 µg) and their control groups. However, the other experimental groups also presented wound contraction albeit milder. At the end of the study, by day 15 wounds from the groups treated with all the lipid nanoparticle formulations had almost closed. Surprisingly, rhEGF-MS 75 µg presented retarded wound contraction (73.16±3.24%) compared with lipid nanoparticles (~95%).

5.4.—Histological Estimation of Wound Healing

On days 8 and 15, animals were killed through $CO_2$ inhalation. The wounds and surrounding tissue (~1 cm) were excised and fixed in 3.7% paraformaldehyde for 24 hours. The fixed tissues were then bisected, embedded in paraffin and excised in 5-µm thick layers. The samples were processed by H&E staining for morphological observations.

Regarding the resolution phases of inflammatory recovery (FIG. 4.A) and wound maturity, the scale described by Cotran et al. (2000) was used (Cotran, R., Kumar, V., Collins, T., 2000. *Reparación de los tejidos: regeneración celular y fibrosis*. Patología estructural y funcional: Mc Graw Hill Interamericana, 2000, pp 95-120). The score of each wound was determined in a semi-quantitative within a range from 0 to 4. 0: Absence of inflammatory response. 1: acute inflammation (formation of the fibrin clot and pyogenic membrane; migration of leucocytes and polynuclear neutrophils), 2: predominance of diffuse acute inflammation (predominance of granulation tissue and pyogenic membrane; vascular neogenesis), 3: predominance of chronic inflammation (fibroblast proliferation), 4: resolution and healing (reduction or disappearance of chronic inflammation although occasional round cells may persist).

The re-epithelization process (FIG. 4.B, D) was measured according to the criteria established by Sinha et al. (Sinha, U.K., Gallagher, L. A., 2003. *Effects of steel scalpel, ultrasonic scalpel, CO2 laser, and monopolar and bipolar electrosurgery on wound healing in guinea pig oral mucosa*. Laryngoscope 113, 228-236). 0: re-epithelization at the edge of the wound, 1: re-epithelization covering less than half of the wound, 2: re-epithelization covering more than half of the wound, 3: re-epithelization covering the entire wound with irregular thickness and 4: re-epithelization covering the entire wound, normal thickness.

5.5.—Statistical Analysis

All data are expressed as the means±standard deviation. Based on the Levene test result of homogeneity of variances, the means were compared through student's t test or one-way ANOVA for multiple comparisons. Subsequently, the Bonferroni or Tamhane post-hoc test was applied. Differences were considered significant at p<0.05. Computations were performed using SPSS 20.0 (SPSS®, Inc., Chicago, Ill.).

By day 8, only rhEGF-SLN 20 µg presented a chronic inflammatory state close to the complete resolution, in which fibroblast proliferation prevailed (score 3.67±1.15)

(Table 6). Animals treated with rhEGF-NLC 20 µg, almost with predominance of acute inflammatory state near to the chronic state, showed less inflammatory score (2.75±0.46). However, these differences were not statistically significant. In addition, both formulations presented significantly greater restoration than their control groups. Conversely, rhEGF-SLN 10 µg and rhEGF-NLC 10 µg did not leave the acute inflammatory state (<2.00); nevertheless, differences (p<0.001) were found among these groups and the untreated control group, which showed absence of inflammatory response. rhEGF-NLC 10 µg also presented differences (p<0.05) with its control (empty NLC).

Regarding the evaluation of dose response (20 or 10 µg) between the lipid nanoparticles, only rhEGF-SLN 20 µg presented an improved resolution (higher than rhEGF-SLN 10 µg).

Histopathological analysis also indicated that in wounds treated with rhEGF prevailed a diffuse acute inflammatory state, with an inflammatory score of 2.13±0.64 (significantly greater than their control groups). These differences did not achieve the statistical significance with any of the lipid nanosphere (neither rhEGF-SLN nor rhEGF-NLC).

As mentioned above, 15 days after wounding differences tend to be lower, not reaching the statistical significance among any group and their controls.

Regarding the re-epithelization grade, by day 8 obtained data showed that only the groups treated with lipid nanoparticles with the highest dose (20 µg) and animals treated with rhEGF-MS 75 µg, presented new epithelium covering more than half of the wound (>2.00, related to the Sinha U.K. (2003) criteria). Moreover, statistically significant differences were found among these groups and their control groups (free rhEGF, empty SLN and untreated control for rhEGF-SLN 20 µg and free rhEGF, empty NLC and untreated control for rhEGF-NLC 20 µg) (FIG. 5). In contrast, in groups treated with lipid nanoparticles with the lower dose of rhEGF (rhEGF-SLN 10 µg and rhEGF-NLC 10 µg), the new epithelium did not overtake more than half of the wound. Furthermore, although significant differences were found with the untreated group (p<0.01), the statistical significance tended to loose with empty SLN in the case of rhEGF-SLN 10 µg, and with empty NLC in the case of rhEGF-NLC 10 µg, even though the re-epithelized scores were higher for the 10 µg rhEGF-loaded lipid nanoparticles (FIG. 4.B). Regarding rhEGF-MS 75 µg, by day 8 the re-epithelized area covered more than half of the wound and statistically significant differences were found among rhEGF-MS 75 µg and its control groups (untreated control and empty MS).

Thus, the study of re-epithelization process (Table 7) revealed that animals treated with 4 doses of 75 µg of free rhEGF showed higher re-epithelization score than untreated groups (1.25±0.89 and 0.00±0.00 respectively). Surprisingly, the effect of multiple intralesional doses of free rhEGF showed less re-epithelization improvement than that obtained from 4 topical administrations of rhEGF-SLN and rhEGF-NLC and 1 intralesional dose of rhEGF-MS 75 µg.

15 days after wound induction the re-epithelization study did not reveal differences among groups.

TABLE 6

Inflammation score

| | Inflammation score | |
|---|---|---|
| | Day 8 | Day 16 |
| Untreated control | 0.13 ± 0.51 | 1.83 ± 0.98 |
| Empty MS | 0.25 ± 0.46 | 2.83 ± 1.33 |
| Empty SLN | 1.25 ± 0.46 | 2.88 ± 0.83 |
| Empty NLC | 1.00 ± 1.10 | 2.50 ± 1.38 |
| Free rhEGF | 1.75 ± 0.71 | 2.75 ± 0.95 |
| rhEGF-MS 75 µg | 2.13 ± 0.64 | 2.86 ± 0.90 |
| rhEGF-SLN 10 µg | 1.63 ± 1.51 | 3.50 ± 0.93 |
| rhEGF-SLN 20 µg | 3.67 ± 1.15 | 3.38 ± 0.52 |
| rhEGF-NLC 10 µg | 1.88 ± 1.21 | 3.13 ± 0.35 |
| rhEGF-NLC 20 µg | 2.75 ± 0.46*, | 3.00 ± 0.00 |

TABLE 7

Re-epithelization score

| | Re-epithelization score | |
|---|---|---|
| | Day 8 | Day 16 |
| Untreated control | 0.00 ± 0.00 | 2.50 ± 1.76 |
| Empty MS | 0.38 ± 0.52 | 3.00 ± 1.10 |
| Empty SLN | 1.00 ± 0.00 | 3.38 ± 0.92 |
| Empty NLC | 1.00 ± 0.89 | 3.00 ± 0.89 |
| Free rhEGF | 1.25 ± 0.89 | 2.71 ± 0.49 |
| rhEGF-MS 75 µg | 2.13 ± 0.64 | 3.17 ± 0.98 |
| rhEGF-SLN 10 µg | 1.71 ± 0.76 | 3.00 ± 0.93 |
| rhEGF-SLN 20 µg | 2.33 ± 0.58 | 3.25 ± 0.71 |
| rhEGF-NLC 10 µg | 1.50 ± 1.05 | 3.38 ± 0.52 |
| rhEGF-NLC 20 µg | 2.75 ± 0.74 | 32.86 ± 0.69 |

Example 6.—In Vivo Wound Healing in Pigs with rhEGF-Loaded NLC 6.1.—Animals

All the protocols and procedures used were previously approved by the Institutional Animal Care and Use Committee from the Jesús Usón Minimally Invasive Surgery Centre (JUMISC). Six female Large White pigs, with a mean weight of 26.82±2.90 kg at the beginning of the study, distributed in individual pens of 2.90 m×1.35 m were used. All the animals of the study were randomly distributed in acclimated rooms, where the following housing conditions were established: 12-hour light-dark cycle, temperature between 20 and 25° C., eight air changes per hour with HEPA-filtered ventilation and relative humidity between 50 and 70%. As pen environmental enrichment, hanging chains and chewing rubber toys were installed as chewable elements. After an acclimatization period, the animals were identified by ear tag codes to be included in the study.

6.2.—Wound Model and Surgical Procedure

After 12 hours of solid and 6 hours of liquid starvation, the animals were sedated through intramuscular administration of 15 mg/kg ketamine and 0.2 mg/kg diazepam. Anaesthesia was then induced by propofol (3 mg/kg) administration to allow endo-tracheal intubation. Immediately after, the animals were connected to an anaesthetic machine through a circular circuit attached to a ventilator supplying sevoflurane as anaesthetic agent at a concentration of 2.7% in an oxygen flow of 1 L/min. As analgesia, remifentanil was used through intravenous infusion in a continuous infusion rate of 0.1 µg/kg/min during the surgery.

To each animal 6 wounds (6 cm×5 cm) were created leaving a minimum of 1.5-2.0 cm between each ulcer, after tattooing the ulcer edges using a frame to have permanent reference of the initial wound area. Ulcers were created using monopolar diathermy in coagulation mode to obtain ischemic wound edges, 2 mm in depth, leaving the panniculus adiposus. Postoperative analgesia was administered through buprenorphine-containing transdermal patches and systemic antibiotic treatment with amoxicillin/clavulanic acid (20 mg/kg) during one week.

6.3.—Experimental Groups

Treatment administration began 24 hours after wound induction (day 1 of the study) to allow primary homeostasis, platelet adhesion and aggregation, and activation of the coagulation cascade. The animals were randomly divided into three groups (n=2): (i) empty NLC, (ii) 20 µg rhEGF-NLC and (iii) 75 µg free rhEGF. Nanoparticles previously resuspended in 150 µl of vehicle (0.5% carboxymethylcellulose in 0.9% saline) were topically administered twice a week by spreading them over the wound bed. Free rhEGF, resuspended in 1 ml of vehicle, was intralesionally administered twice a week.

Throughout the study, the wounds were covered to avoid dehydration and microbial contamination. Moreover, dressing prevented scab formation and facilitated observation of the epithelized edges for area measurements of the healed wounds. To this end, each wound was covered with a paraffin gauze to avoid bandage adhesion, on top three sterile cotton gauzes were placed, fixed with an adhesive bandage and a sticking plaster. Dressings were changed twice per week to continually assess the state and evolution of the wound, maintaining this way a high aseptic level. The cleaning process was carry out with the greatest care, using sterile gauzes and saline solution to eliminate exudates and detritus, respecting the integrity of the newly formed granulation tissue.

6.4.—Blood Samples

To monitor the general health status of the animals, blood samples were collected to check the haematological and biochemical levels on the day of the wound induction, on day 15 and at the end of the study (day 43). The studied parameters were: haematocrit, haemoglobin, mean corpuscular volume (MCV), mean corpuscular haemoglobin (MCH), white blood cells, total proteins and platelets.

In addition, plasma samples from the rhEGF-NLC and free rhEGF treated animals were collected to assess rhEGF systemic absorption. rhEGF detection was performed by ELISA (human EGF ELISA development kit, PeproTech). Samples were drawn when the plasma rhEGF levels were expected to be higher. Thus, samples from the animals treated with rhEGF-NLC were collected on day 1 of the experiment (prior to the treatment administration), 4 hours and 24 hours after administration. Plasma samples from the animals treated with free rhEGF were obtained just after administration and 30 minutes after the first dose.

6.5.—Serial Wound Analysis of Healed Wounds

Wound healing kinetic was determined by measuring the wound closure (percentage of initial wound area closed) on days 1, 15, 25, 36 and 43. The wound area was assessed, in a standardized manner, taken photographs perpendicularly to the wound surface, using the same illumination and placing a transparent plastic sterile ruler next to the wounds to introduce a metric reference in the pictures for further processing. The wound area was calculated using the image software ImageJ (see section 5.3). The wounds were considered healed when closure was above 95%.

6.6.—Histological Assessment of Wound Healing

Complete skin thickness biopsies from the centre of the unhealed wound to the healthy margin (2 mm) were collected using a sterile scalpel. Collected samples were immediately fixed in 4% formalin, embedded in paraffin and excised in 5-µm thick layers. Samples were stained with haematoxilyn-eosin (HE) for morphological observations. Biopsies were collected on day 15 for wounds 1, 2 and 3 and on days 25 and 43 for all of the wounds. On day 36, wound images were taken but no biopsies were collected not to delay wound healing.

Wound healing was determined in terms of the re-epithelization grade by measuring the newly formed epithelia, and wound maturity and healing quality according to the Cotran et al. (2000) criteria.

6.7.—Haematology Analysis

The haematology analysis did not reveal any change in none of the studied parameters throughout the study. In addition, all the obtained values were within the normal ranges for healthy pigs (data not shown).

Plasma samples of the animals treated with rhEGF-NLC and free rhEGF were collected to assess rhEGF absorption into the systemic circulation when the rhEGF concentration was expected to be higher in plasma, because the systemic use of rhEGF has been limited by the concern of abnormal epithelial growth. The plasma collection time points were chosen based on the EGF half-life, the administration route and the delayed release of the growth factor loaded in the rhEGF-NLC. In this regard, because the rhEGF incorporated into rhEGF-NLC was expected to be absorbed later than free rhEGF due to encapsulation, plasma sampling was performed on day 1 of the experiment, 4 hours and 24 hours after rhEGF-NLC administration, instead of 30 minutes after administration, as performed with the animals treated with free rhEGF.

Due to human and pig marked similarities, similar rhEGF plasma concentrations were expected. As illustrated in Table 8, the rhEGF plasma concentration showed values of approximately 0, clearly bellow basal human EGF concentration (0.4 ng/ml). This fact is very striking because the virtually nonexistence of systemic absorption, even when free rhEGF is directly injected into the wound, may minimize the site effects; and therefore, improve treatment safety and ensure rhEGF local effect in the lesion.

TABLE 8 rhEGF plasma concentrations. The data are shown as the means ± S.D.

| | rhEGF plasma concentrations (ng/ml) | | |
|---|---|---|---|
| | 30 minutes | 4 hours | 24 hours |
| rhEGF-NLC | — | 0.03 ± 0.01 | 0.01 ± 0.01 |
| Free rhEGF | 0.20 ± 0.01 | — | — |

6.8.—Serial Wound Analysis of Healed Wounds

Enhanced healing was evaluated by calculating the number of healed wounds in each experimental group on days 15, 25, 36 and 43. The greatest differences among the groups were found on day 25 of the experiment. As depicted in FIG. 8, by day 15 none of the wounds had completely closed. By day 25 the percentage of healed wounds were significantly higher for the rhEGF-NLC treated group than for the empty NLC treated group. In addition, it should be pointed out that treatment with rhEGF-NLC showed a slight superior effectiveness compared with free rhEGF (50% and 40%, respectively). Although the percentage of healed wounds were similar in both groups, these data are particularly significant as the wounds treated with rhEGF-NLC received two weekly topical administrations of 20 µg of rhEGF, while those wounds treated with free rhEGF received higher doses (75 µg twice a week) intralesionally administered. By day 36, almost all the wounds had healed completely; the wounds treated with rhEGF (both with rhEGF-NLC and free rhEGF) were completely closed and the wounds treated with empty NLC reached 90% healing. At the end of the study (day 43) all the wounds were completely healed.

6.9.—Histological Assessment of Wound Healing
6.9.1.—Re-Epithelization Grade

As shown in FIG. 9A, by day 15 the length of the new epithelia was significantly greater in the animals treated with 20 µg rhEGF-NLC topically administered than in those wounds treated with empty NLC and those receiving 75 µg free rhEGF intralesionally administered (p<0.001). The improved re-epithelization effectiveness of rhEGF-NLC compared with free rhEGF, suggests that nanoencapsulation protects the growth factor against the wound microenvironment and reduces the inactivation exerted by the proteases and oxidative stress of the wound area. This protection may be responsible for the enhanced effectiveness of rhEGF-NLC observed in the in vivo studies. However, the differences among the groups did not reach the statistical significance on days 25 y 43 (FIG. 9A), even though the mean values obtained by day 25 for those animals treated with rhEGF (free or encapsulated) were higher than those for the empty NLC group.

6.9.2.—Wound Maturity and Healing Quality

Due to the extent of the created lesions, in the same histological sample different healing stages can be observed according to the Cotran et al. (2000) criteria. As depicted in FIG. 10A, by day 15 the animals treated with rhEGF-NLC showed not only a statistically significant lower extension of inflammatory tissue (Grade 2) compared with those wounds receiving empty NLC and free rhEGF, but also a significantly higher extension of almost completely healed epidermis (Grade 4) (p<0.001). In contrast, empty NLC and free rhEGF treated wounds mainly showed a diffuse acute inflammation with presence of some polymorphonuclear neutrophils, granulation tissue formation and vascular neogenesis (Grade 2).

By day 25, because the healing process continued in all the studied groups, the extension of grade 2 was significantly smaller than that observed on day 15 and the extension of grade 3 and grade 4 significantly higher (p<0.001). In addition, it is noteworthy that even though on day 25 differences in the re-epithelisation length among the groups could not be found, differences were still appreciated in wound maturity and healing quality (FIG. 9A and FIG. 10B). The animals treated with rhEGF-NLC showed a healing grade closer to complete healing than those groups receiving empty NLC and free rhEGF, which still showed chronic inflammation and a granulation tissue rich in new vessels and fibroblast proliferation.

In addition, as shown in FIG. 9B and FIG. 10C, by day 43 all the wounds of all the experimental groups showed some chronic inflammation (grade 3 and 4). However, lesions treated with rhEGF-NLC presented a significantly improved healing grade and wound maturity (p<0.001).

The invention claimed is:

1. Lipid nanoparticle comprising at least one solid lipid at room temperature, at least one non-ionic surfactant, at least one liquid lipid at room temperature, and a growth factor,
   wherein the growth factor is epidermal growth factor (EGF);
   wherein the solid lipid at room temperature is selected from the group consisting of glyceryl palmitostearate, glyceryl monostearate, glyceryl behenate, and mixtures thereof;
   wherein the liquid lipid at room temperature is selected from the group consisting of mixture of triglyceride of caprylic acid and capric acid, soybean oil, isopropyl myristate, castor oil, and mixtures thereof; and
   wherein the non-ionic surfactant is selected from the group consisting of sorbitan esters, polyethoxylated sorbitan esters, polyethylene-polypropylene glycol, and mixtures thereof.

2. Lipid nanoparticle according to claim 1, where the epidermal growth factor is recombinant human epidermal growth factor (rhEGF).

3. Composition characterized by comprising a lipid nanoparticle according to claim 1 and a lipid nanoparticle comprising at least one solid lipid at room temperature, at least one non-ionic surfactant, and a cathelicidin antimicrobial peptide LL37.

4. A medicament comprising a lipid nanoparticle according to claim 1.

5. Pharmaceutical composition comprising a lipid nanoparticle according to claim 1, and a pharmaceutically acceptable carrier.

6. Pharmaceutical composition comprising a composition according to claim 3, and a pharmaceutically acceptable carrier.

7. Pharmaceutical composition according to claim 5, for its use in promoting wound healing in a subject.

8. Kit comprising a lipid nanoparticle according to claim 1.

9. The lipid nanoparticle according to claim 1, wherein the nanoparticle is lyophilized.

10. The pharmaceutical composition according to claim 5, wherein the pharmaceutical composition is in the form of a patch or dressing.

11. Composition characterized by comprising a lipid nanoparticle according to claim 1 and a lipid nanoparticle comprising at least one solid lipid at room temperature, at least on liquid lipid at room temperature, at least one non-ionic surfactant, and the cathelicidin antimicrobial peptide LL37.

12. Pharmaceutical composition comprising a composition according to claim 11, and a pharmaceutically acceptable carrier.

13. The lipid nanoparticle according to claim 1, wherein the at least one solid lipid comprises glyceryl monostearate, the at least one liquid lipid comprises soybean oil, and the non-ionic surfactant comprises polyethylene-polypropylene glycol.

14. The lipid nanoparticle according to claim 1, wherein the at least one solid lipid comprises glyceryl behenate, the at least one liquid lipid comprises isopropyl myristate, and the non-ionic surfactant comprises a mixture of polyethylene-polypropylene glycol and polyethoxylated sorbitan esters.

15. A method of promoting wound healing in a subject comprising using a lipid nanoparticle according to claim 1.

16. The method according to claim 15, wherein the wounds are selected from the group consisting of diabetic foot ulcers, pressure ulcers, vascular ulcers, ischemic wounds, and combinations thereof.

17. Method for the preparation of the lipid nanoparticle according to claim 1, comprising the following steps:
   (i) preparing an aqueous solution comprising a non-ionic surfactant,
   (ii) preparing a lipophilic solution comprising a blend of solid lipids and liquid lipids melted at a temperature higher than the melting point of the liquid lipid,
   (iii) heat the aqueous solution (i) up to the same temperature than the lipophilic solution (ii),
   (iv) adding the aqueous solution (i) to the lipophilic solution (ii), subjecting the resulting mixture to sonication until obtaining an emulsion,
   (v) cooling down the emulsion (iv) at 5° C.±3° C. to allow lipid recrystallization and nanoparticle formation, and
   (vi) collecting the nanoparticles,
   wherein EGF is added to the solution (ii), and
   wherein the solid lipid at room temperature, the liquid lipid at room temperature, and
   the non-ionic surfactant are as defined in claim 1.

* * * * *

SEQUENCE LISTING

```
<160> NUMBER OF SEQ ID NOS: 1

<210> SEQ ID NO 1
<211> LENGTH: 37
<212> TYPE: PRT
<213> ORGANISM: Artificial Sequence
<220> FEATURE:
<223> OTHER INFORMATION: synthetic polypeptide

<400> SEQUENCE: 1

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35
```